US008126690B2

(12) United States Patent
Higgins et al.

(10) Patent No.: US 8,126,690 B2
(45) Date of Patent: Feb. 28, 2012

(54) ALGORITHMS TO PREDICT CLINICAL RESPONSE, ADHERENCE, AND SHUNTING WITH THIOPURINES

(75) Inventors: Peter Higgins, Ann Arbor, MI (US); Ji Zhu, Ann Arbor, MI (US); Akbar Waljee, Ann Arbor, MI (US); Sijian Wang, Ann Arbor, MI (US); Joel Joyce, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1062 days.

(21) Appl. No.: 11/804,366

(22) Filed: May 18, 2007

(65) Prior Publication Data

US 2008/0288227 A1 Nov. 20, 2008

(51) Int. Cl.
*G06G 7/58* (2006.01)
*G01N 33/48* (2006.01)

(52) U.S. Cl. ........................................ 703/11; 702/19

(58) Field of Classification Search ........................ None
See application file for complete search history.

(56) References Cited

U.S. PATENT DOCUMENTS

| | | | |
|---|---|---|---|
| 5,506,213 A | 4/1996 | Carson et al. | |
| 7,189,693 B2 | 3/2007 | Jeffers et al. | |
| 7,767,395 B2 * | 8/2010 | Garrett et al. | 435/6 |

OTHER PUBLICATIONS

Glas et al. Eur J Med Res (2006) 10: 535-538.*

Cuffari et al. Clinical Gastroenterology and Hepatology, vol. 2, Issue 5, May 2004, p. 410 (Abstract).*

JP Achkar et al., "Indicators of Clinical Response to Treatment with six-mercaptopurine or azatholoprine in patients with inflammatory bowel disease," Inflamm Bowel Disease, Jul. 2004, Abstract.

Benjamin A. Goldenberg et al., "The Utility of 6-Thioguanine Metabolite Levels in Managing Patients with Inflammatory Bowel Disease," American Journal of Gastroenterology, 2004, pp. 1744-1748.

Carmen Cuffari et al., "Thiopurine Methyltransferase Activity Influences Clinical Response to Azathioprine in Inflammatory Bowel Disease," Clinical Gastroenterology and Hepatology, May 2004, pp. 410-417, American Gastroenterological Association.

Marla C. Dubinsky et al., "Pharmacogenomics and Metabolite Measurement for 6-Mercaptopurine Therapy in Inflammatory Bowl Disease," Gastroenterology, 2000, vol. 118, pp. 705-713, American Gastroenterological Association, Montreal, Canada.

Glas J. et al., "The leukocyte count predict the efficacy of treatment with azathioprine in inflammatory bowel disease." Eur. J. Med. Res., Dec. 7, 2005, Abstract.

Lloyd Mayer, "When is too much enough?" Gastroenterology, Apr. 2006, vol. 130, No. 4. pp. 1352-1354.

Thomas CW, Jr. et al. "Erthrocyte mean corpuscular volume as a surrogate marker for 6-thioguanine nucleotide concentration monitoring in patents with inflammatory bowel disease treated with azathioprine or 6-mercaptopurine," Inflamm Bowel Disease, Jul. 2003, Abstract.

Mark T. Osterman et al., "Association of 6-Thioguanine Nucleotide Levels and Inflammatory Bowel Disease Activity: A Meta-Analysis," American Gastroenterological Association, Apr. 2006, vol. 130, pp. 1047-1053.

Marla C. Dubinsky et al., "6-Mp Metobolite Profiles Provide a Biochemical Explanation for 6-MP Resistance in Patients with Inflammatory Bowel Disease," American Gastroenterological Association, Apr. 2002, pp. 904-915.

Max Reinshagen et al., "6-Thioguanine Nucleotide-Adapted Azathioprine Therapy Does Not Lead to Higher Remission Rates than Standard Therapy in Chronic active Crohn Disease: Results from A Randomized Controlled, Open Trial" Clinical Chemistry 2007, 53:7; pp. 1306-1314.

Pierre-Nicolas D'Halluin et al., "RBC 6-TGN and hematological parameters in patients with Crohn's disease treated by azathioprine," Gastroenterol Clin. Biol. 2005, vol. 29, pp. 1264-1269.

International Search Report issued Sep. 30, 2008 I corresponding PCT/US2008/063973, 3 pages.

Written Opinion issued Sep. 30, 2008 I corresponding PCT/US2008/063973, 5 pages.

* cited by examiner

*Primary Examiner* — Michael Borin
(74) *Attorney, Agent, or Firm* — Marshall, Gerstein & Borun LLP

(57) ABSTRACT

A method of using a variable set from complete blood counts and blood chemistry panels to generate a machine learned algorithm for determining the effectiveness of thiopurine treatment on inflammatory bowel disease (IBD) patients using CART, boosted trees, random forest classification, RuleFit and/or logistic regression analysis.

9 Claims, 40 Drawing Sheets

Table: Defining Clinical Responders and Non-Responders for Crohn's Disease

| Clinical Non-Responders | Clinical Responders |
|---|---|
| 1. A modified Harvey Bradhsaw Index (mHBI) >= 4 on or off steroids, or, | 1. CD patients must have been in remission as defined by a mHBI < 4, off steroids, and no open fistulae for at least 3 weeks |
| 2. A mHBI <4, but still requiring steroids for maintenance of remission (steroid-dependent), or, | |
| 3. The presence of draining fistulas for fistulizing patients. | |

Figure 2

Table: Defining Clinical Responders and Non-Responders for Ulcerative Colitis

| Clinical Non-Responders | Clinical Responders |
|---|---|
| 1. A modified Ulcerative colitis Disease Activity Index (mUCDAI) >=4 on or off steroids, or, | 1. UC patients must have been in remission as defined by an mUCDAI < 4 off steroids. |
| 2. A mUCDAI < 4, but still requiring steroids for maintenance of remission (steroid-dependent), or, | |
| 3. The presence of draining fistulas for fistulizing patients. | |

Figure 3

1a. Clinical Response Prediction --- CART (AUC=0.722)

2a. Noncompliance Prediction --- CART (AUC = 0.525)

3a. Shunt Prediction --- CART (AUC = 0.628)

1b. Clinical Response Prediction --- Boosting (AUC=0.821)

% Importance Of Clinical Predictors for Clinical Response

| Input | Value |
|---|---|
| baso | 0 |
| tbil | 0.424457832 |
| bicarbonate | 0.426327539 |
| mono | 0.514266108 |
| chlor | 0.526189275 |
| creat | 0.735708052 |
| cal | 1.161595949 |
| prot | 1.201050325 |
| ast | 1.489095829 |
| lymph | 1.647075714 |
| mcv | 1.766099549 |
| mpv | 1.83076068 |
| sod | 2.040301266 |
| alt | 2.079895023 |
| mchc | 2.159120493 |
| hbg | 3.102980079 |
| eos | 3.683747286 |
| wbc | 3.697007781 |
| pot | 3.725946765 |
| plt | 4.484221031 |
| mch | 5.374962142 |
| un | 5.924201634 |
| gluc | 6.074486039 |
| alb | 6.756870398 |
| age | 7.326550576 |
| alk | 9.716761799 |
| rdw | 10.05319578 |
| neut | 12.07712506 |

Figure 12

2b. Noncompliance Prediction --- Boosting (AUC = 0.806)

% Importance Of Clinical Predictors for Non-Compliance

| Input | Value |
|---|---|
| eos | 0 |
| baso | 0.011341507 |
| pot | 0.099634973 |
| mono | 0.132716478 |
| chlor | 0.144009438 |
| alb | 0.240207902 |
| neut | 0.339413569 |
| plt | 0.556507368 |
| sod | 1.060927675 |
| alt | 1.196051246 |
| tbil | 1.211816283 |
| wbc | 1.291676455 |
| cal | 1.310905423 |
| creat | 1.321620384 |
| mchc | 2.319215879 |
| un | 2.774504284 |
| lymph | 4.005379181 |
| rdw | 4.081827679 |
| gluc | 4.375599717 |
| ast | 4.969242909 |
| mch | 5.295513194 |
| bicarbonate | 5.31184545 |
| prot | 5.945785803 |
| alk | 6.259150802 |
| age | 8.889140821 |
| mcv | 11.09916715 |
| hbg | 12.46100069 |
| mpv | 13.29579774 |

Figure 15

3b. Shunt Prediction --- Boosting (AUC = 0.729)

% Importance Of Clinical Predictors for Shunting

| Input | Value |
|---|---|
| baso | 0.00025948 |
| chlor | 0.337414573 |
| bicarbonate | 0.583908735 |
| wbc | 1.005293796 |
| ast | 1.273331356 |
| prot | 1.313672994 |
| sod | 1.359260363 |
| eos | 1.402749797 |
| cal | 1.43196014 |
| mono | 1.838588291 |
| un | 1.841306376 |
| pot | 2.380061814 |
| lymph | 2.440783215 |
| mcv | 2.879372872 |
| tbil | 2.891760324 |
| mchc | 3.049268649 |
| alb | 3.050000048 |
| gluc | 3.175673699 |
| rdw | 3.844852089 |
| hbg | 4.46859045 |
| neut | 5.093099502 |
| plt | 5.904674492 |
| alk | 6.34333277 |
| alt | 6.46643982 |
| creat | 6.997153713 |
| mpv | 7.317141471 |
| mch | 9.730321647 |
| age | 11.57972752 |

Figure 18

% Importance Of Clinical Predictors for Clinical Response

| Input | Value |
|---|---|
| neutrophil count | 8.48 |
| alkaline phosphate | 7.45 |
| red cell distribution width | 5.68 |
| age | 5.65 |
| white blood cell count | 5.31 |
| platelets | 4.77 |
| hemoglobin | 4.77 |
| albumin | 4.66 |
| glucose | 4.64 |
| eosinophils | 3.66 |
| aspartate transaminase | 3.61 |
| mean cell hemoglobin concentrat | 3.61 |
| potassium | 3.22 |
| urea nitrogen | 3.21 |
| protein | 3.01 |
| mean cell hemoglobin | 2.82 |
| mean cell volume | 2.74 |
| sodium | 2.68 |
| lymphocyte count | 2.68 |
| mean platelet volume | 2.63 |
| monocytes | 2.52 |
| alanine transaminase | 2.39 |
| calcium | 2.24 |
| bicarbonate | 2.12 |
| chloride | 2.01 |
| creatinine | 1.8 |
| total bilirubin | 1.33 |
| basophils | 0.31 |

Figure 20

% Importance Of Clinical Predictors for Non-Compliance

| Input | Value |
|---|---|
| mean platelet volume | 11.68 |
| hemoglobin | 9.66 |
| mean cell volume | 5.93 |
| protein | 5.1 |
| mean cell hemoglobin | 4.99 |
| white blood count | 4.71 |
| bicarbonate | 4.18 |
| lymphocyte count | 4.12 |
| mean cell hemoglobin concentrat | 3.86 |
| age | 3.67 |
| red cell distribution width | 3.53 |
| neutrophils | 3.52 |
| platelets | 3.41 |
| urea nitrogen | 3.29 |
| alkaline phosphotase | 3.19 |
| creatinine | 2.74 |
| aspartate transaminase | 2.53 |
| alanine transaminase | 2.31 |
| glucose | 2.23 |
| albumin | 2.17 |
| monocytes | 2.15 |
| total bilirubin | 2.1 |
| chloride | 2 |
| calcium | 1.81 |
| sodium | 1.72 |
| potassium | 1.45 |
| eosinophils | 1.33 |
| basophils | 0.61 |

Figure 23

% Importance of Clinical Predictors For Shunting

| Input | Value |
|---|---|
| creatinine | 7.59 |
| age | 7.14 |
| mean plate volume | 5.86 |
| alanine transferase | 5.75 |
| platelet | 5.27 |
| hemoglobin | 4.69 |
| neutrophils | 4.55 |
| mean cell volume | 4.47 |
| red cell distribution width | 4.31 |
| white blood cell count | 4.29 |
| mean cell hemoglobin | 4.28 |
| alkaline phosphatase | 4.18 |
| asparatate transaminase | 3.51 |
| calcium | 3.35 |
| albumin | 3.34 |
| total bilirubin | 3.24 |
| lymphocyte count | 3.18 |
| mean cell hemoglobin concentrat | 2.83 |
| glucose | 2.73 |
| sodium | 2.45 |
| protein | 2.34 |
| potassium | 2.21 |
| monocytes | 2.12 |
| urea nitrogen | 1.8 |
| bicarbonate | 1.6 |
| chloride | 1.59 |
| eosinophils | 1.15 |
| basophils | 0.19 |

Figure 26

1. Clinical Response Prediction (AUC=0.870)

% Importance of Clinical Predictors For Clinical Response

| Input | Value |
|---|---|
| neut | 20.26831921 |
| rdw | 9.661081128 |
| alk | 9.452986596 |
| age | 8.011569363 |
| alb | 6.915090145 |
| un | 6.033478292 |
| gluc | 4.666041307 |
| eos | 3.802102365 |
| pot | 3.656754928 |
| prot | 3.380090672 |
| plt | 3.245875367 |
| lymph | 2.926135379 |
| hbg | 2.804214532 |
| mch | 2.550064918 |
| sod | 2.150921789 |
| bicarbonate | 2.08332403 |
| mchc | 1.94698474 |
| wbc | 1.550390987 |
| mcv | 1.418522556 |
| mpv | 1.32425187 |
| cal | 1.132778452 |
| tbil | 0.545187069 |
| alt | 0.309428117 |
| creat | 0.063488116 |
| mono | 0.050059658 |
| chlor | 0.027151046 |
| ast | 0.023707364 |
| baso | 0 |

Figure 30

2. Noncompliance Prediction (AUC=0.761)

% Importance of Clinical Predictors For Non-Compliance

| Input | Value |
|---|---|
| mpv | 23.99846609 |
| hbg | 16.2975165 |
| age | 11.33943133 |
| rdw | 7.442381092 |
| co2 | 6.339286178 |
| prot | 6.136034005 |
| un | 5.025755194 |
| mcv | 4.95090591 |
| lymph | 3.806401101 |
| tbil | 3.488261481 |
| creat | 2.787606574 |
| gluc | 2.401361662 |
| alt | 1.894764228 |
| neut | 1.476300738 |
| sod | 0.818335222 |
| alb | 0.713058114 |
| ast | 0.497936905 |
| wbc | 0.299585955 |
| mch | 0.286611718 |
| plt | 0 |
| mchc | 0 |
| baso | 0 |
| pot | 0 |
| alk | 0 |
| mono | 0 |
| chlor | 0 |
| cal | 0 |
| eos | 0 |

Figure 33

3. Shunt Prediction (AUC=0.764)

% Importance of Clinical Predictors For Shunting

| Input | Value |
|---|---|
| age | 16.94045897 |
| creat | 12.23728718 |
| mpv | 11.58646084 |
| alt | 9.139412093 |
| neut | 8.733423296 |
| mch | 5.135420809 |
| plt | 4.393816846 |
| alk | 3.81518627 |
| mcv | 3.583147623 |
| rdw | 3.000739377 |
| hbg | 2.906177979 |
| alb | 2.898100635 |
| wbc | 2.773092901 |
| ast | 2.330085386 |
| mchc | 1.691684144 |
| gluc | 1.624502683 |
| prot | 1.163016107 |
| mono | 1.151729728 |
| tbil | 0.970496995 |
| sod | 0.76289155 |
| lymph | 0.690434402 |
| cal | 0.679913249 |
| bicarbonate | 0.444224649 |
| eos | 0.416528762 |
| pot | 0.349286972 |
| chlor | 0.299754362 |
| un | 0.282726193 |
| baso | 0 |

Figure 36

Table: Clinical Response with General Labs

| Variable | Odds Ratio | 95% Confidence Intervals | | p-value |
|---|---|---|---|---|
| WBC | 0.754 | 0.678 | 0.838 | 0 |
| RDW | 0.804 | 0.723 | 0.894 | 0 |
| EOS | 8.051 | 1.298 | 49.958 | 0.025 |
| Alb | 2.903 | 1.64 | 5.138 | 0 |
| Age | 0.972 | 9.533 | 0.992 | 0.005 |

number of observations = 395 area under ROC curve = 0.8038

Figure 37

Table: Noncompliance with General Labs

| Variable | Odds Ratio | 95% Confidence Intervals | | p-value |
|---|---|---|---|---|
| WBC | 1.756 | 1.279 | 2.411 | 0.001 |
| Age | 1.049 | 1.029 | 1.07 | 0 |
| MCH | 0.666 | 0.553 | 0.802 | 0 |
| NEUT | 0.578 | 0.394 | 0.846 | 0.005 |
| RDW | 0.656 | 0.489 | 0.879 | 0.005 |

number of observations = 774 area under ROC curve = 0.8031

Figure 38

Table: Shunters with General Labs

| Variable | Odds Ratio | 95% Confidence Intervals | | p-value |
|---|---|---|---|---|
| EOS | 0.104 | 0.137 | 0.794 | 0.029 |
| Creat | 0.059 | 0.006 | 0.558 | 0.014 |
| LYMPH | 1.518 | 1.126 | 2.047 | 0.006 |
| MCH | 1.149 | 1.04 | 1.27 | 0.006 |

number of observations = 716 area under ROC curve = 0.6903

Figure 39

ALGORITHMS TO PREDICT CLINICAL RESPONSE, ADHERENCE, AND SHUNTING WITH THIOPURINES

BACKGROUND OF THE INVENTION

Inflammatory bowel disease (IBD) patients frequently require thiopurine therapy to achieve remission. Thiopurines are widely used immunomodulators which have proven benefits in inflammatory bowel disease (IBD) patients who have failed 5-aminosalicylic acid (5-ASA) compound treatment. These immunomodulators can effectively induce both clinical and endoscopic remission, are steroid-sparing, and have even been shown to have benefit in fistulizing Crohn's disease. Unfortunately, thiopurines have a narrow therapeutic index, and their pharmacokinetics vary widely between individuals. Rare patients with low levels of the enzyme thiopurine methyltransferase (TPMT) are at significant risk of severe bone marrow suppression and patients with very high levels of TPMT are unlikely to respond to thiopurines. Traditionally, the balance between efficacy and risk with thiopurines has been managed by experienced physicians monitoring results of a complete blood count (CBC) and chemistry panels as well as overall clinical symptoms. These experienced, or expert, physicians use a gestalt impression of how a few of the variables in the CBC and chemistry panels should look when a patient is responding or not responding to the thiopurine treatment. However, there is no evidence that this subjective approach is effective and because this approach is dependent on expert assessment, the approach is difficult to reproduce.

Recently, a more reproducible approach to thiopurine risk management and evaluation of clinical efficacy has used the monitoring of 6-thioguanine (6-TGN) and 6-methylmercaptopurine (6-MMP) metabolites. Measurement of metabolites compensates for the individual patient variation in metabolism (pharmacokinetics) of thiopuine medications. 6-TGN is an active metabolite, and high levels correlate with good clinical response. 6-MMP is a shunt metabolite, and patients who shunt to 6-MMP are less likely to benefit from thiopurine treatment, and may actually develop liver toxicity. Specifically, 6-TGN levels greater than 230 pmol/10e8 RBCs are associated with clinical response, and 6-MMP levels greater than 5700 pmol/10e8 RBCs are associated with an increased risk of hepatoxicity. However, a recent meta-analysis of studies of these metabolites shows that their sensitivity for clinical response is only 62 percent and their specificity is only 72 percent. Additionally, monitoring these metabolites tests are costly, and slow (e.g., typical time to yield results is 5 days).

There remains a need in the art for inexpensive and accurate tests to determine probability of clinical response to thiopurine therapy, probability of patient adherence to (or conversely non-compliance with) the thiopurine treatment regimen, and probability of patient shunting of thiopurines to inactive metabolites. There is evidence that in addition to the pharmacokinetic variation between patients in their metabolism of thiopurines, there is also substantial variation in the pharmacodynamics of thiopurines between patients. This variation in the therapeutic effect of a given amount of drug or metabolite on the individual can not be predicted by metabolite testing.

SUMMARY OF THE INVENTION

The claimed method and system uses statistical tree regression and classification tree techniques to determine the importance of variables used in a full blood count and chemistry and to produce an algorithm based on those variables to predict the effectiveness of thiopurine treatment, or clinical response, with good sensitivity and specificity. The set of conditions may be coded as a computer program used to calculate clinical response, adherence, and shunting, and the results may appear as probability values displayed on a screen or printed on paper. Computing systems programmed to implement these algorithms are also contemplated. The statistical regression and classification tree techniques may include CART (or single tree), boosted trees, random forest analysis, or RuleFit alone or in combination with multivariate logistic regression analysis.

Generally, clinical response refers to a clinical condition of a patient in which the thiopurines are therapeutically effective (i.e., having the desired effect on suppressing the patient's immune system). Probability of clinical response can be an indicator of the adequacy of the treatment dosage. Adherence or compliance refers to whether a patient is following treatment, i.e., actually taking the prescribed medication according to schedule. Shunting occurs when a patient is not metabolizing the thiopurine drug along the correct metabolic path; a high probability of shunting indicates that the patient is likely not going to benefit from the thiopurine drug and may even have increased likelihood of toxicity.

BRIEF DESCRIPTION OF THE DRAWINGS

FIGS. 2 and 3 illustrate tables showing criteria indicating clinical response and non-response;

FIG. 12 illustrates a variable importance table including the values for the set of inputs shown in FIG. 11;

FIG. 15 illustrates a variable importance table including the values for the set of inputs shown in FIG. 15;

FIG. 18 illustrates a variable importance table including the values for the set of inputs shown in FIG. 17;

FIG. 20 illustrates a variable importance table including the values for the set of inputs shown in FIG. 19;

FIG. 23 illustrates a variable importance table including the values for the set of inputs shown in FIG. 22;

FIG. 26 illustrates a variable importance table including the values for the set of inputs shown in FIG. 25;

FIG. 30 illustrates a variable importance table including the values for the set of inputs shown in FIG. 29;

FIG. 33 illustrates a variable importance table including the values for the set of inputs shown in FIG. 32;

FIG. 36 illustrates a variable importance table including the values for the set of inputs shown in FIG. 35;

FIG. 37 illustrates the results of a logistic regression to determine clinical response;

FIG. 38 illustrates the results of a logistic regression to determine adherence;

FIG. 39 illustrates the results of a logistic regression to determine shunting.

DETAILED DESCRIPTION

Figure 1:
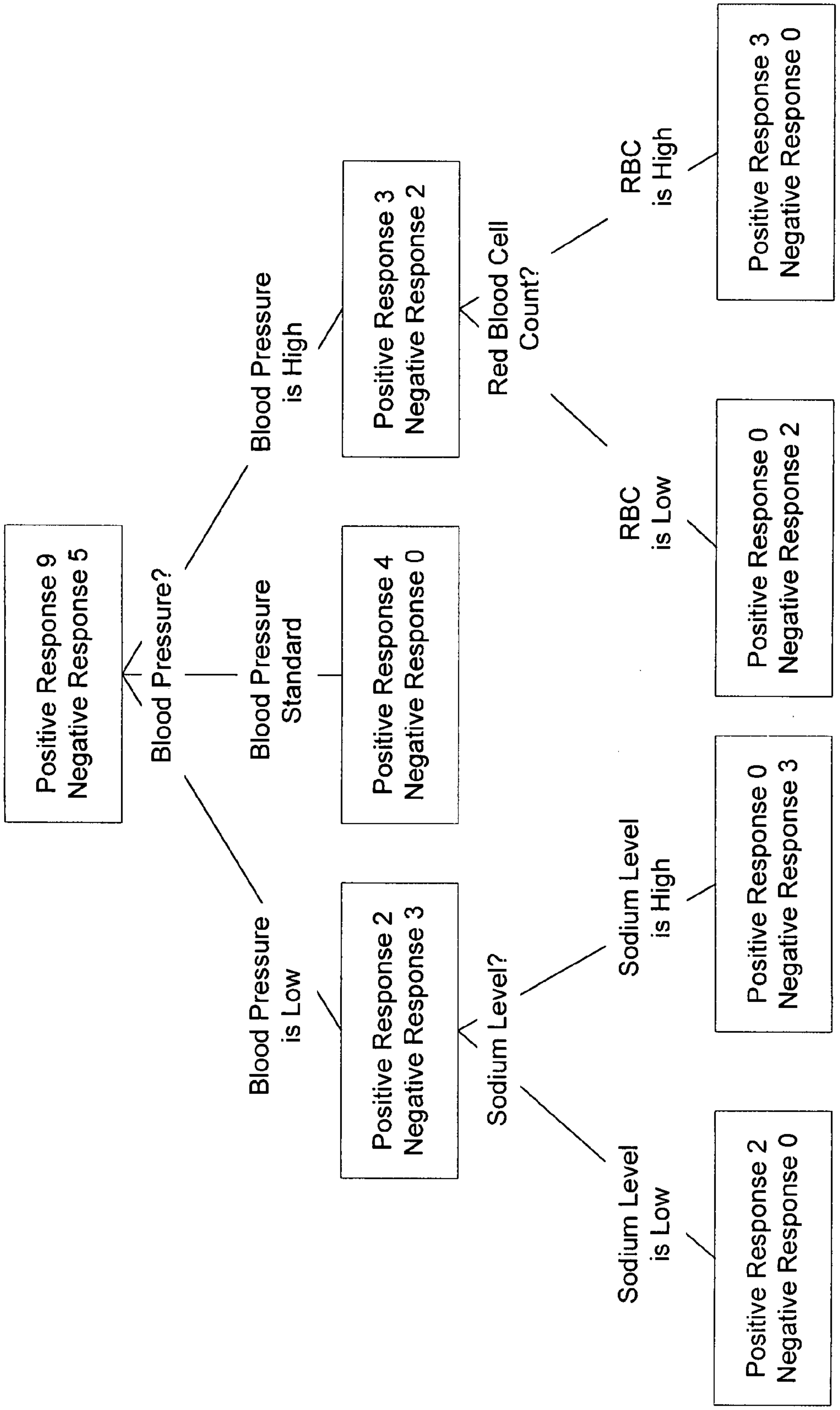
FIG. 1 illustrates a classification tree example for a different disease unrelated to the present invention (effect of medication on heart disease)

Although the following text sets forth a detailed description of numerous different embodiments, it should be understood that the legal scope of the invention is defined by the words of the claims set forth at the end of this patent. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term '__________' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

In general, the aim of diagnostic or prognostic testing is to predict the result (e.g. diagnose a condition or likelihood of response to a medication) with accuracy. There are several parameters to measure how well a test performs. Sensitivity is the proportion of true positive subjects (subjects with the condition) who test positive with the screening test. Similarly, specificity is defined as the proportion of true negative subjects (subjects without the condition) who test negative with the screening test. The Area Under the Receiver Operating Characteristic curve (AuROC) is another way of representing the overall accuracy of a test and ranges between 0 and 1.0, with an area of 0.5 representing test accuracy no better than chance alone. Higher AuROC indicates a better performance.

Traditionally, the effectiveness of thiopurine treatment on inflammatory bowel disease (IBD) patients may be assessed by experienced physicians viewing results of standard blood work. In particular, two variables are primarily relied upon in making these "expert" assessments: mean corpuscular volume (MCV) and white blood cell count for a patient. The rationale behind using white blood cell count is that a patient's white blood cell count may be related to effects on bone marrow, and levels too low may indicate an impact of the thiopurine treatment such that the dosage of thiopurine may need to be reduced or completely stopped; conversely, levels too high may indicate insufficient effect such that the drug may need to be increased. Similarly, if the patient's red blood cell volume is not within certain "intuitive" tolerances, then the change in the patient's condition may also require dosage adjustment. For example, two studies have shown that increasing red blood cell size is correlated with the levels of 6-TGN metabolites, and other studies have shown that these correlate with a positive clinical response. However, the correlation of the change in red blood cell size (delta MCV) with clinical response was not shown. The ability of this single-variable approach to predict clinical response has not been quantified or documented. Moreover, because trained physicians are required to provide the gestalt assessment of "sufficient" increases in red blood cell size and decreases in white blood cell count, this method is not easily reproduced.

Currently, monitoring of 6-thioguanine (6-TGN) and 6-methylmercaptopurine (6-MMP) metabolites provides a more quantitative test in monitoring the effectiveness of thiopurine treatment. This approach may be characterized as an attempt to estimate the clinical response of a patient to the thiopurine treatment by studying secondary factors influencing the metabolism or breakdown of the applied thiopurine. These factors are secondary because they do not directly indicate clinical response of a patient to the treatment. To summarize, the current industry trend in monitoring thiopurine effectiveness is primarily based on measuring MCV, white blood cell count, and the metabolites 6TGN and 6MMP. Currently, the measurement of 6-TGN and 6-MMP are considered useful when attempting to determine medical noncompliance and may be helpful for optimizing dose and monitoring for toxicity per the guidelines of the American Gastroenterological Association Contrary to the existing trend in the art to use secondary factors in estimating immunological response to thiopurine treatment, the inventors of the present application quantified the importance of variables included in the complete variable set provided by a complete blood work and blood chemistry panels to determine algorithms for determining the effect of thiopurine treatment on the immune system.

Pharmacodynamics is the study of how drugs affect the body after they are absorbed and metabolized. Some drugs have substantial variation in their pharmacodynamics. It appears that thiopurines are in this category also. Measuring metabolites captures the variation in pharmacokinetics. However, it does not capture the variation in pharmacodynamics. Measuring the effects on the immune system (blood counts) and blood chemistries (which are the inputs in our algorithms) captures both the variation in pharmacokinetics and the variation in pharmacodynamics between individuals. It is one step closer on the causative pathway from drug to clinical response, and therefore will be a better predictor of clinical response.

It should be noted that, before the present application, physicians were not able to effectively provide a quantifiable and/or reproducible method for determining the effects of thiopurine treatment based on blood work alone. Moreover, the "expert" assessments were primarily based on a subset of variables from a complete blood count (i.e., MCV and white blood cell count). The importance of other variables in their assessment have been largely unrecognized.

Classification And Regression Tree Methods

Generally, classification or regression trees are used to predict membership of cases or objects in the classes of a categorical dependent variable from the measurements of one or more predictor variables (or independent variables). In other words, a decision tree may be used as a predictive model which maps observations about an item to conclusions about the item's target value. In these tree structures, leaves represent classifications and branches represent conjunctions of features that lead to those classifications.

FIG. 1 is included to illustrate an example of using a classification tree used to determine a dependent variable: effectiveness of a heart medication (i.e., whether a patient responds positively or negatively to the medication). The data set includes the following independent (or measured) predictor variables: blood pressure (i.e., whether a patient's blood pressure is high, normal, or low), sodium level (i.e., whether a patient has a high or low sodium level), and red blood cell count (i.e., whether a patients red blood cell count is high or low). As illustrated in FIG. 1, the classification and regression tree is complete in the sense that it has correctly categorized each case with 100 percent accuracy for the independent variable. The classes include low blood pressure and low sodium level, low blood pressure and high sodium level, standard blood pressure, high blood pressure low red blood cell count and high blood pressure high red blood cell count. The result is that patients respond well when they have normal blood pressure, low blood pressure and low sodium level, or high blood pressure and high red blood cell count. The simplified classification and regression tree example provides a method for determining response of patients to a medication. When appropriately constructed (e.g., after the tree is first built on initial learning data) the tree may also be used to produce a set of if-then logical (split) conditions that permit accurate prediction or classification of later case data. In other words, a set of if-then conditions may be produced based on the tree to represent an algorithm for predicting a dependent variable.

The process of computing classification and regression trees can be characterized as involving four basic steps: 1) specifying the criteria for predictive accuracy; 2) selecting splits; 3) determining when to stop splitting; and 4) selecting the size of the tree. Different approaches to classification and regression tree analysis differ in the manner in which one or more of the basic steps is handled. The standard classification and regression tree (CART) approach, for example, uses a single tree, much like the example provided above. More sophisticated approaches involve multiple trees or variations in technique on splitting, weighting, size selection, etc. (some further techniques to be discussed below).

The claimed method system may use a standard classification and regression tree (CART) approach (using a single classification tree) to develop a first set of algorithms for three dependent variables of interest in analyzing thiopurine treatment: clinical response, noncompliance, and shunting to 6-MMP (rather than metabolism to 6-TGN). The CART learning algorithm may be trained on a set of data using actual medical records. A sample training set may include around 395 cases that indicate the clinical response outcome of the patients. Patients with CD or Ulcerative Colitis/Intermediate Colitis may be classified as responders (clinical remission), non-responders or unknown responders using the clinical criteria established by Dubinsky et al., "6-MP metabolite profiles provide a biochemical explanation for 6-MP resistance in patients with inflammatory bowel disease," Gastroenterology 2002; 122:904-15. The tables in FIGS. 2 and 3 illustrate the criteria that may be used to classify patients for the clinical response outcome.

Noncompliance may be defined as a 6-TGN level less than 25 and a 6-MMP level less than 25, as it is rare for patients on 25 mg of azathioprine daily (the lowest recorded dose in our dataset) to have a 6-TGN level less than 30. Shunting may be defined a priori as a 6-TGN/6-MMP ratio less than 20 in patients who had 6-TGN levels greater than 25.

The independent or predictor variables may be derived from complete blood count values, blood chemistries, patient age. Patient age may be calculated as the number of years between the date of birth of a patient and the date of a laboratory draw at which thiopurine metabolites was obtained for the patient.

The complete blood count may include any set of the following independent variables: hemoglobin, hematocrit, red blood cell count, white blood cell count, platelet count, mean cell volume (MCV), mean cell hemoglobin (MCH), mean cell hemoglobin concentration (MCHC), mean platelet volume (MPV), neutrophil count (NEUT), basophil (BASO) count, monocyte count (MONO), lymphocyte count (LYMPH), and eosinophil count (EOS).

The chemistries may include any set of the following independent variables: aspartate aminotransferase (ASP), alanine aminotransferase (ALT), alkaline phosphatase (ALK), bilirubin (TBIL), calcium (CAL), albumin (ALB), sodium (SOD), potassium (POT), chloride (CHLOR), bicarbonate, blood urea nitrogen (UN), creatinine (CREAT), and glucose (GLUC).

It should be noted that since steroids can alter some of the common laboratory parameters (e.g., raise glucose, decrease eosinophils), and steroids may be a part of the outcome definition of Dubinsky, there may be a danger of circular reasoning in any regression model development (e.g., steroid use could alter laboratory values which would differentiate steroid use/failure of thiopurines). Therefore, the algorithms developed in this application may also be tested to determine if they are effective to differentiate clinical responders from nonresponders in the subset of patients not on steroids.

Clinical Response

Generally, clinical response indicates the effectiveness of the thiopurine treatment in reducing IBD in patients. As discussed above, technical criteria for clinical response may be based on validated Dubinsky data, which is illustrated in FIGS. 2 and 3. The CART method may be trained based on the laboratory values in a random training set of 70% of the cases, where the resulting algorithms may then be tested on the remaining 30% of the cases.

Figure 4:
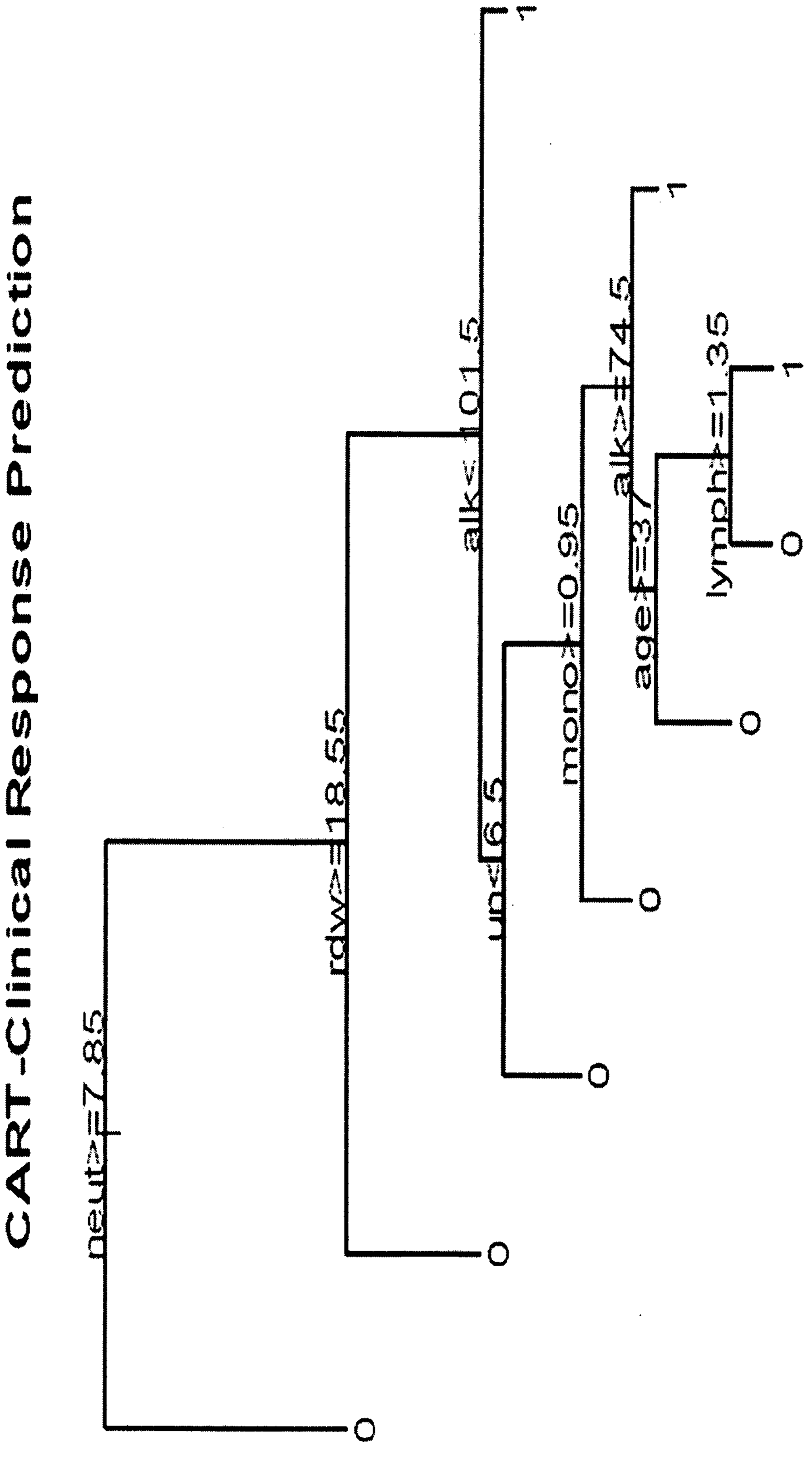
FIG. 4 illustrates a CART tree for clinical response.
Figure 5:
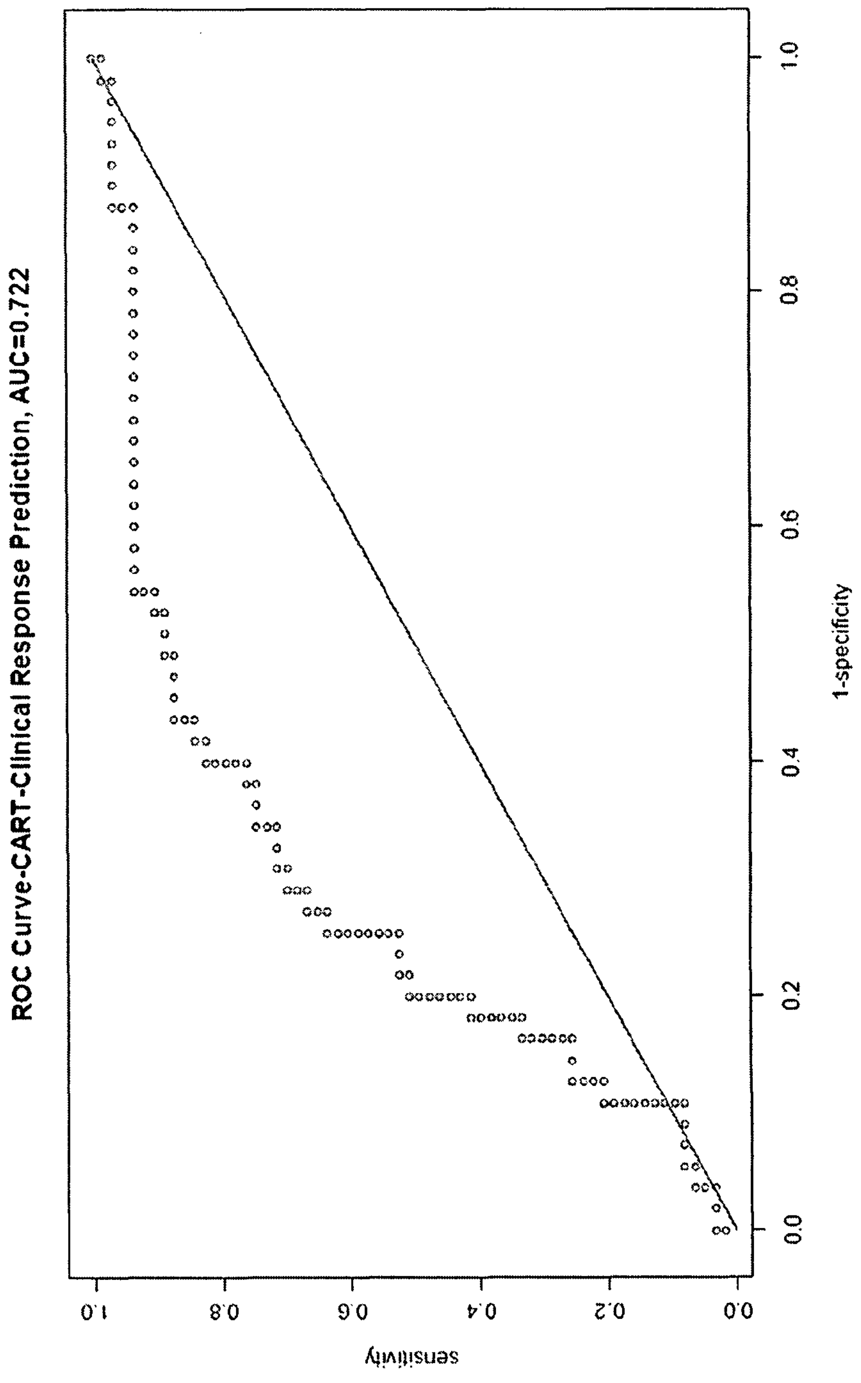
FIG. 5 illustrates an AuROC graph of the CART algorithm for clinical response.
Figure 6:
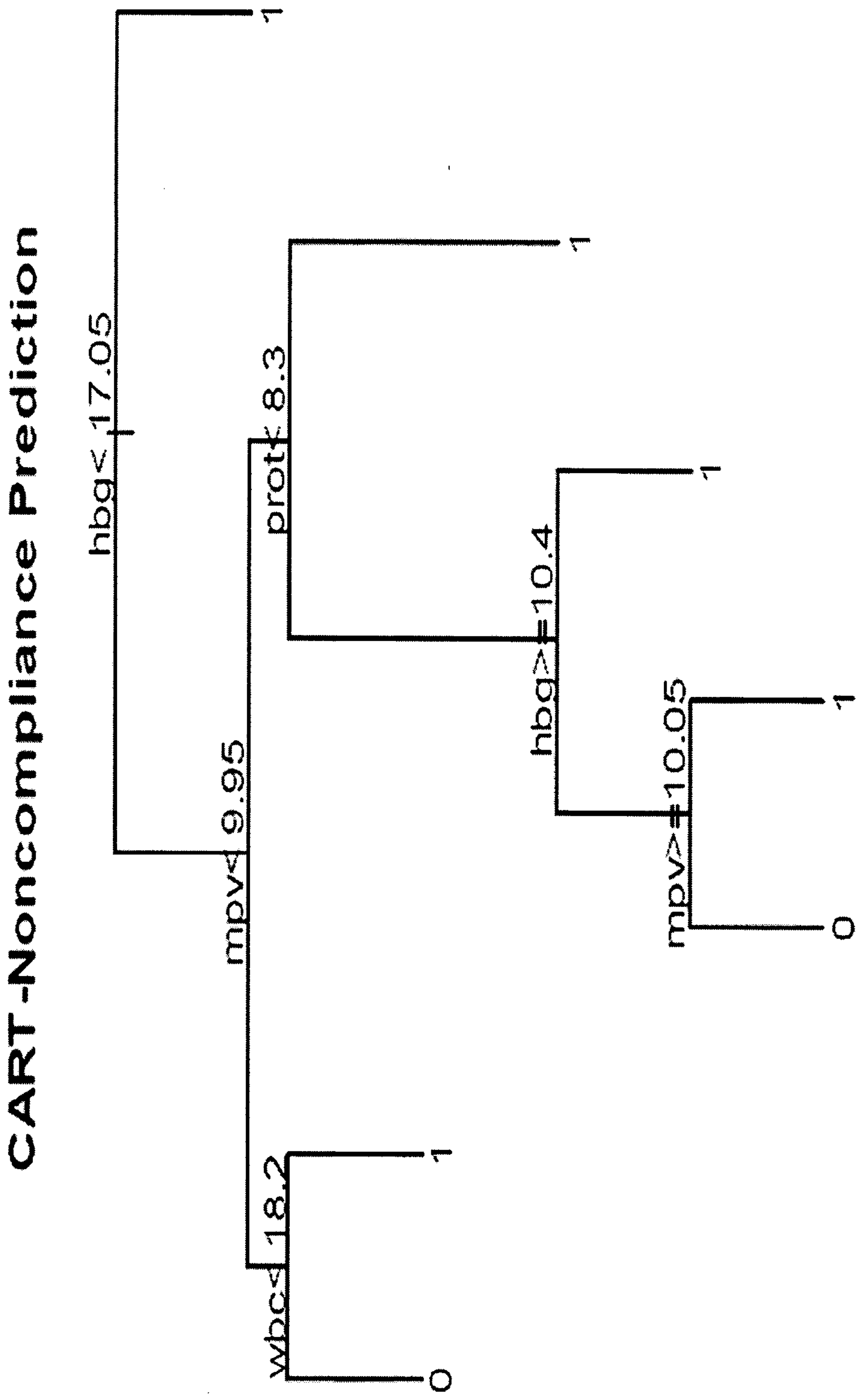
FIG. 6 illustrates a CART tree for adherence.
Figure 7:
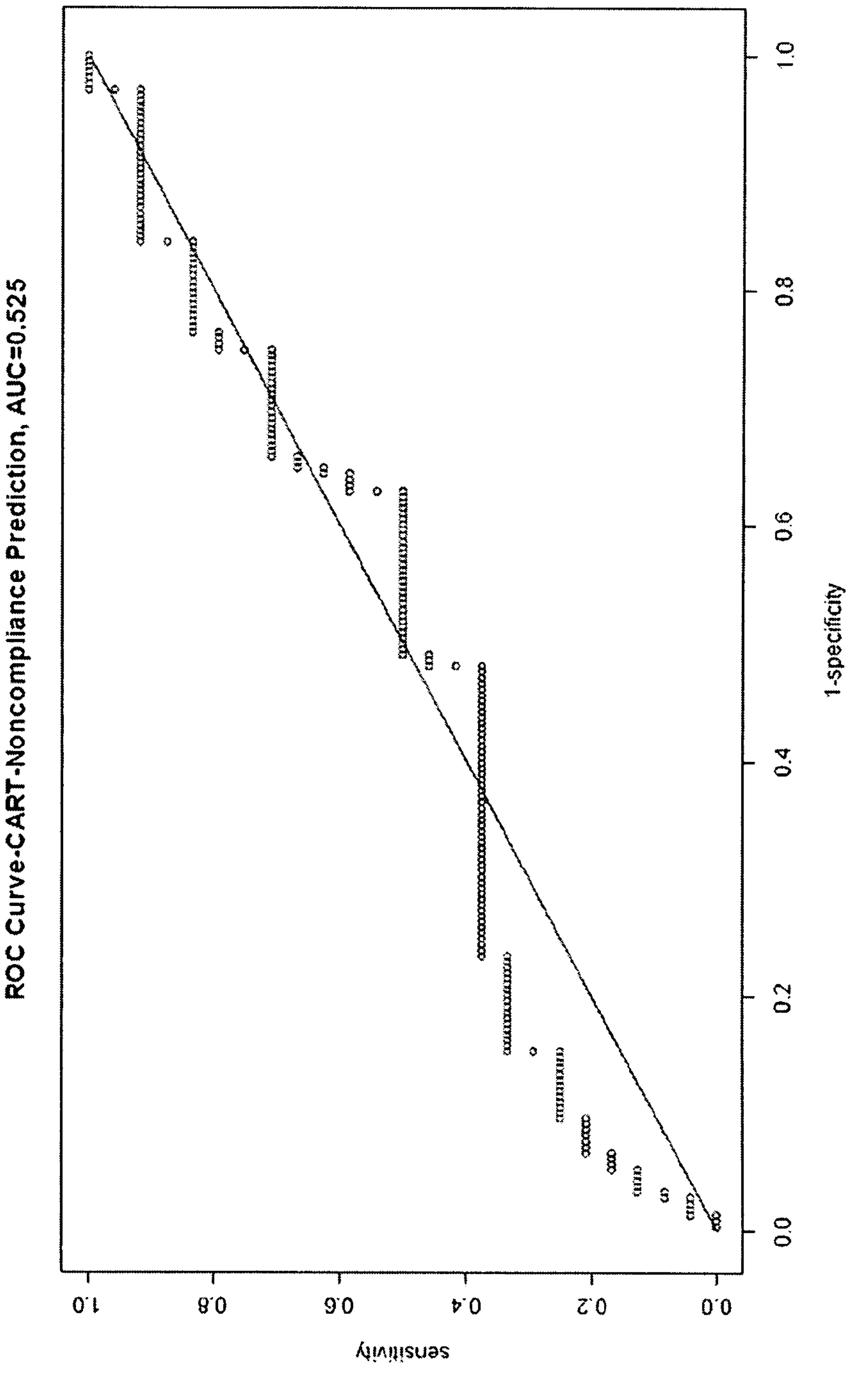
FIG. 7 illustrates an AuROC graph of the CART algorithm for adherence.
Figure 8:
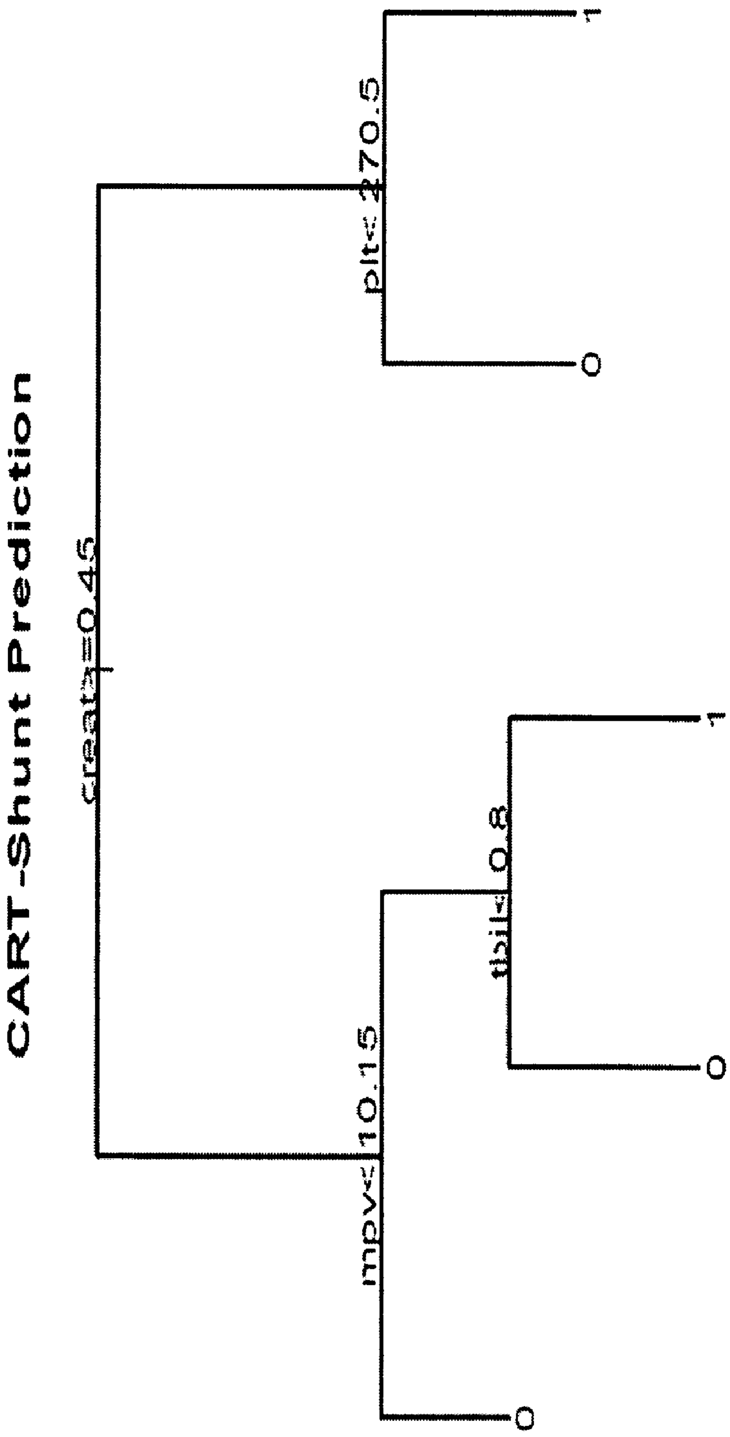
FIG. 8 illustrates a CART tree for shunting.
Figure 9:
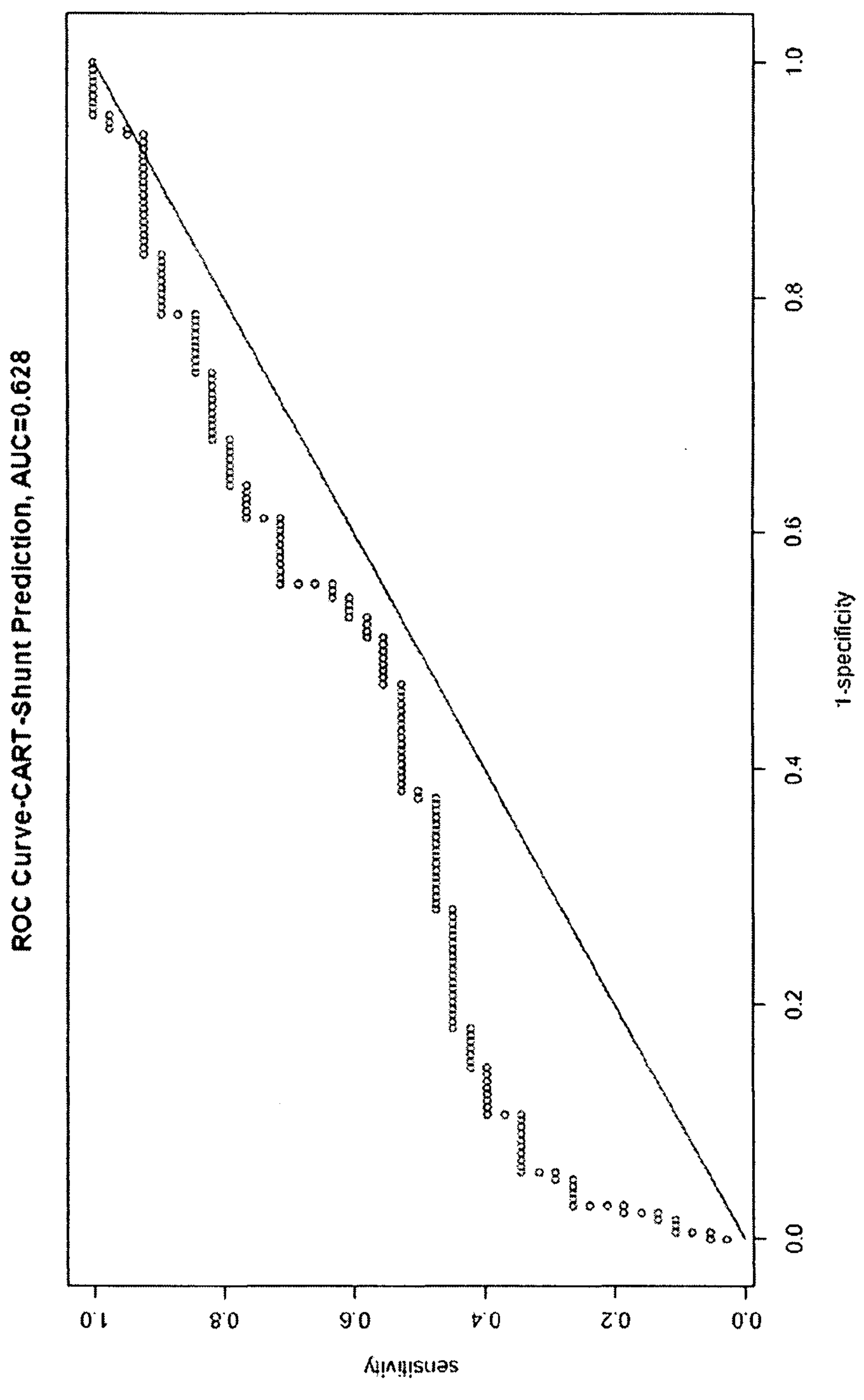
FIG. 9 illustrates an AuROC graph of the CART algorithm for shunting.

The CART approach may be used to produce the tree model illustrated in FIG. 4 that has an area under receiver operating characteristic (AuROC) curve of 0.722 for clinical response as illustrated in FIG. 5. This AuROC represents greater effectiveness than the metabolite tests. The CART approach may also be used to produce the tree model of adherence (FIG. 6) with an AuROC of 0.525 (FIG. 7) and a tree model of shunting (FIG. 8) with an AuROC of 0.628 (FIG. 9). The single tree CART method demonstrates that the inputs (i.e., the independent variables) are relevant in predicting clinical response.

To produce better models/algorithms and to further determine variable importance, enhanced classification and regression tree approaches may be used on the same variable set. For example, boosted trees, random forest, and Rule Fit may be used.

A tree boosting approach combines a set of weak classifier variables (e.g., hemoglobin and white blood cell count) to achieve a final powerful classifier. This is done by constructing an initial decision tree based on the model development data to classify the dependent variable (i.e. clinical response). For all cases in the development data set in which the outcome is mis-classified, the weight of these cases is increased (boosted), and a new decision tree is generated to optimize classification of the outcome based on the new case weights. The mis-classified cases again have their weights boosted, and a new decision tree is generated. This approach is repeated iteratively, typically hundreds or thousands of times, until an optimal boosted tree is identified. This boosted decision tree is then applied to the validation data set, and cases in the validation data set are classified as responders or nonresponders.

A random forest approach is an ensemble method that combines many decision trees, typically 10,000. These trees are grown differently from those in the tree boosting approach in that: (1) instead of weighting the training cases, the method randomly selects, with replacement, n samples from the original training data; (2) instead of considering all input variables at each split of the decision tree, a small group of input variables on which to split are randomly selected; and (3) each tree is grown to the largest extent possible. To classify a new case as a responder or nonresponder, one runs the input case data (i.e. white blood cell count, mean cell volume, etc.) through each of the trees in the forest. Each tree gives a classification (vote). The random forest approach selects the classification having the most votes over all the trees in the forest. The random forest has several beneficial properties: like boosting, it is robust with respect to input variable noise and overfitting, and it gives estimates of which variables are important in the classification.

RuleFit is another method of using ensembles of decision trees to achieve optimal classification of outcomes from predictor variables. It is similar to the random forest approach, but its output may not typically produce a large number of trees, e.g., 10,000 trees. Instead, the most common and most effective splitting rules ("branch points") are identified across the ensemble of trees, and the output is a set of splitting rules. This form of output is usually slightly less accurate than the model with 10,000 trees (in the range of about 1-5%), but is much simpler to convert to programming language like C++ or SQL code and apply to future observations to predict outcomes.

Tree Boosting Approach

Figure 10:
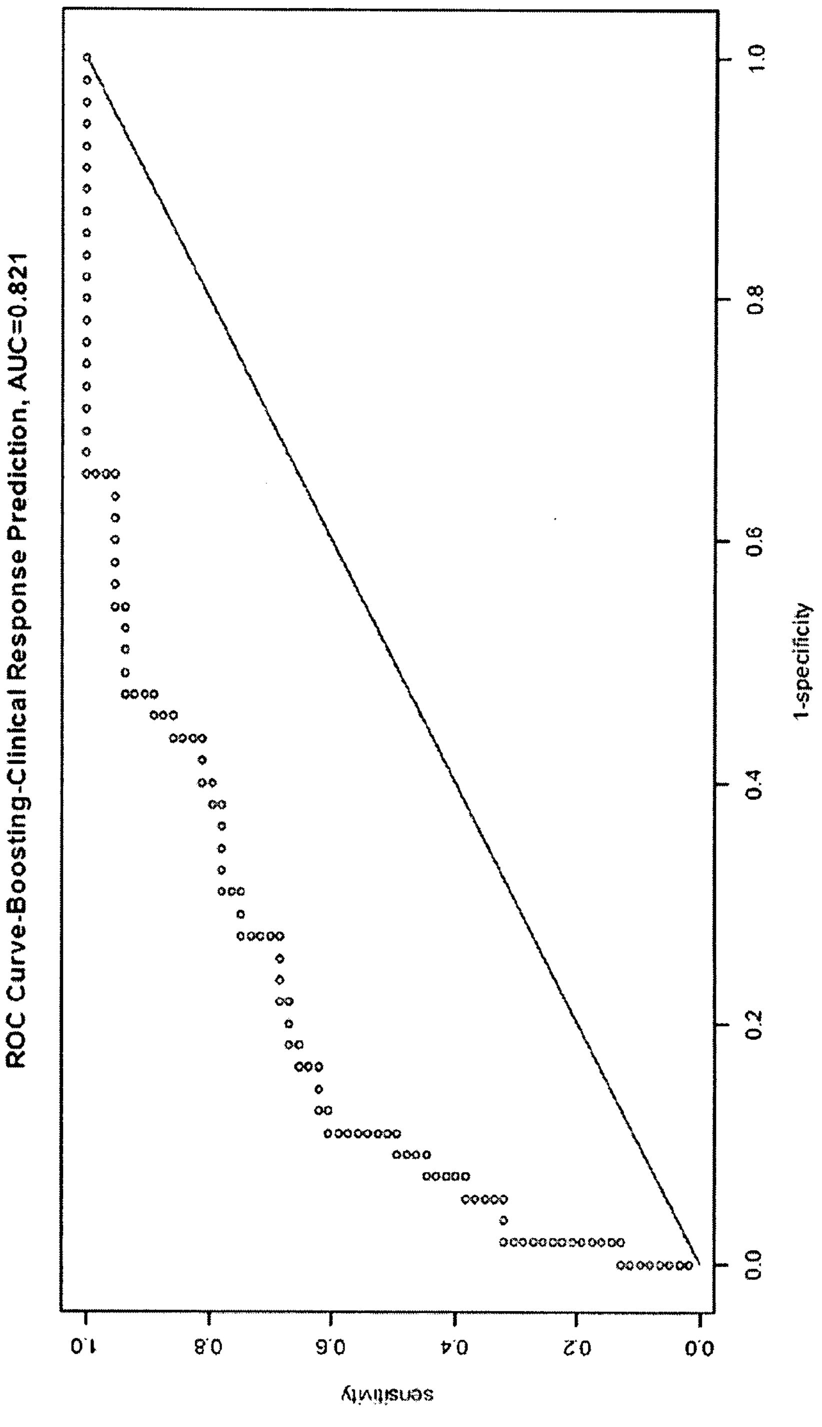
FIG. 10 illustrates an AuROC graph of the boosted trees algorithm for clinical response.
Figure 11:
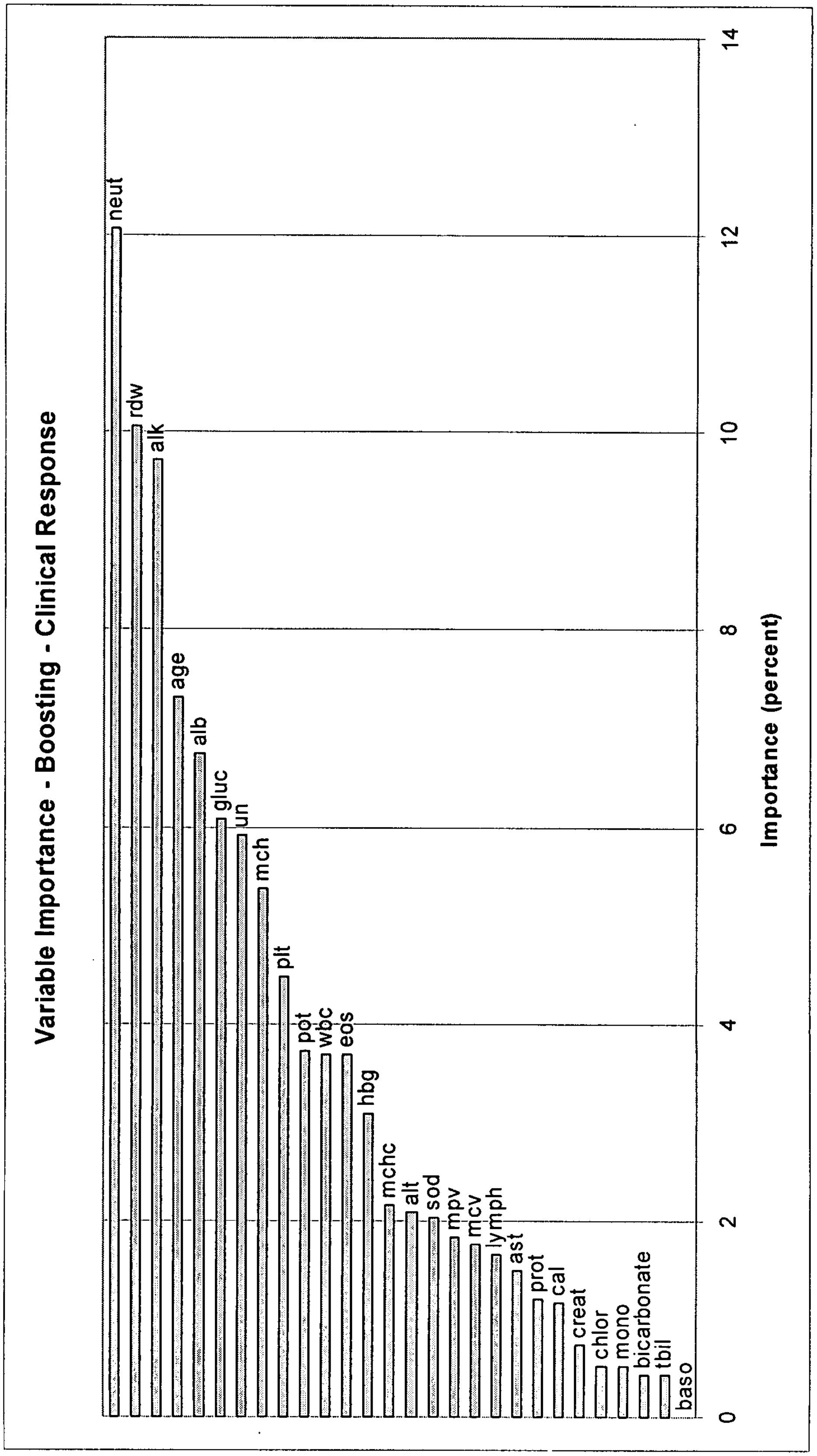
FIG. 11 illustrates a variable importance graph for a set of inputs identifying the boosted trees algorithm for clinical response.
Figure 13:
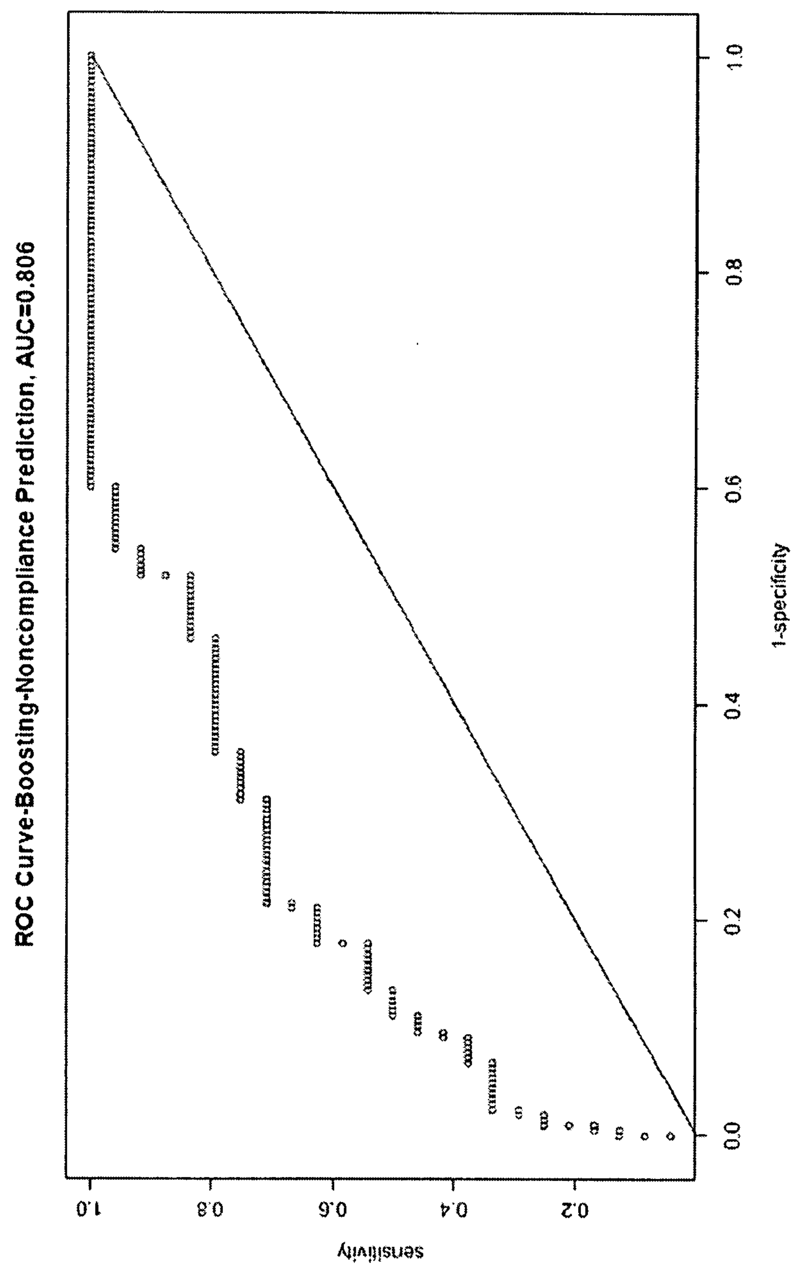
FIG. 13 illustrates an AuROC graph of the boosted trees algorithm for adherence.
Figure 14:
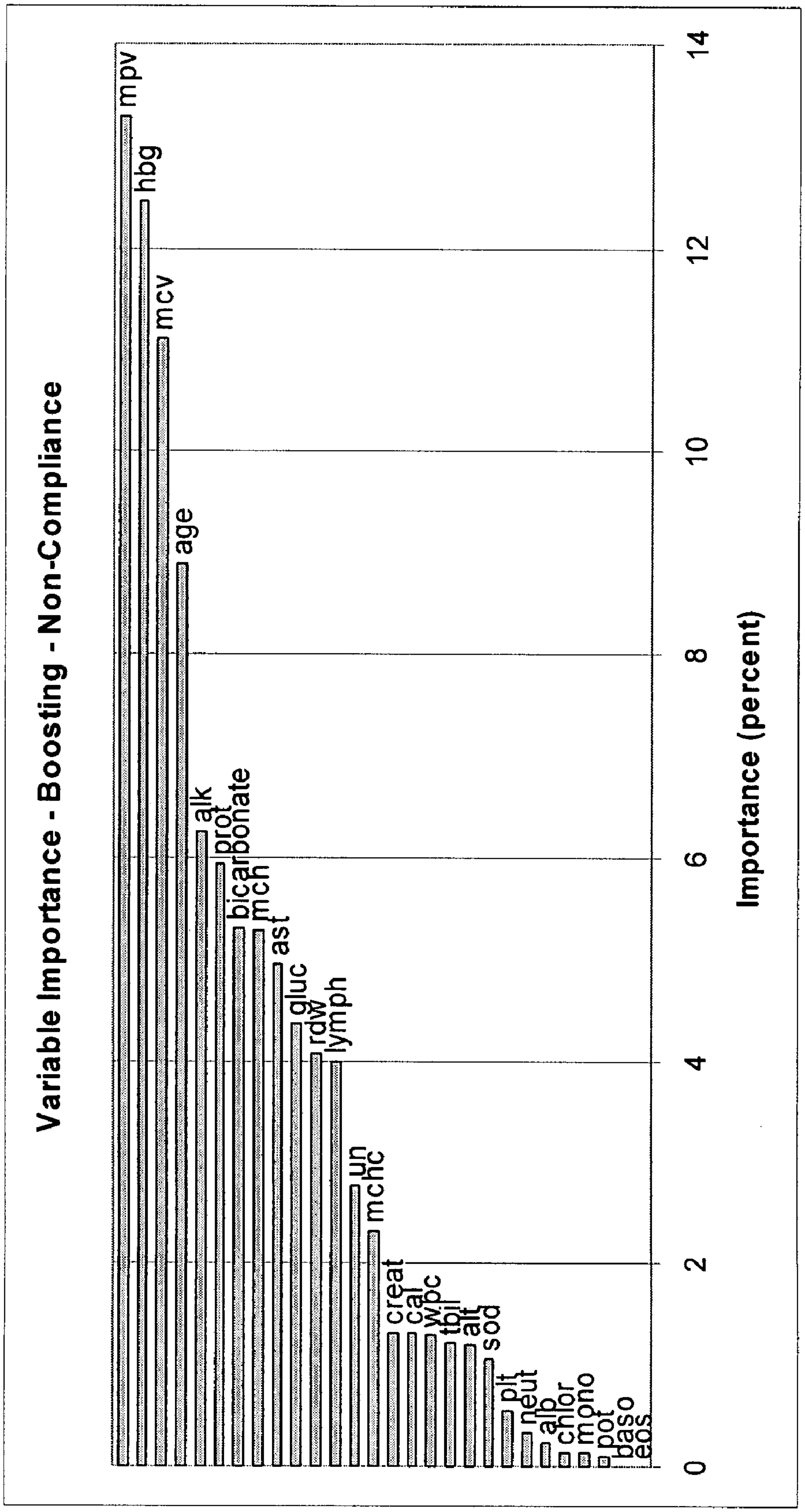
FIG. 14 illustrates a variable importance graph for a set of inputs identifying the boosted trees algorithm for adherence.
Figure 16:
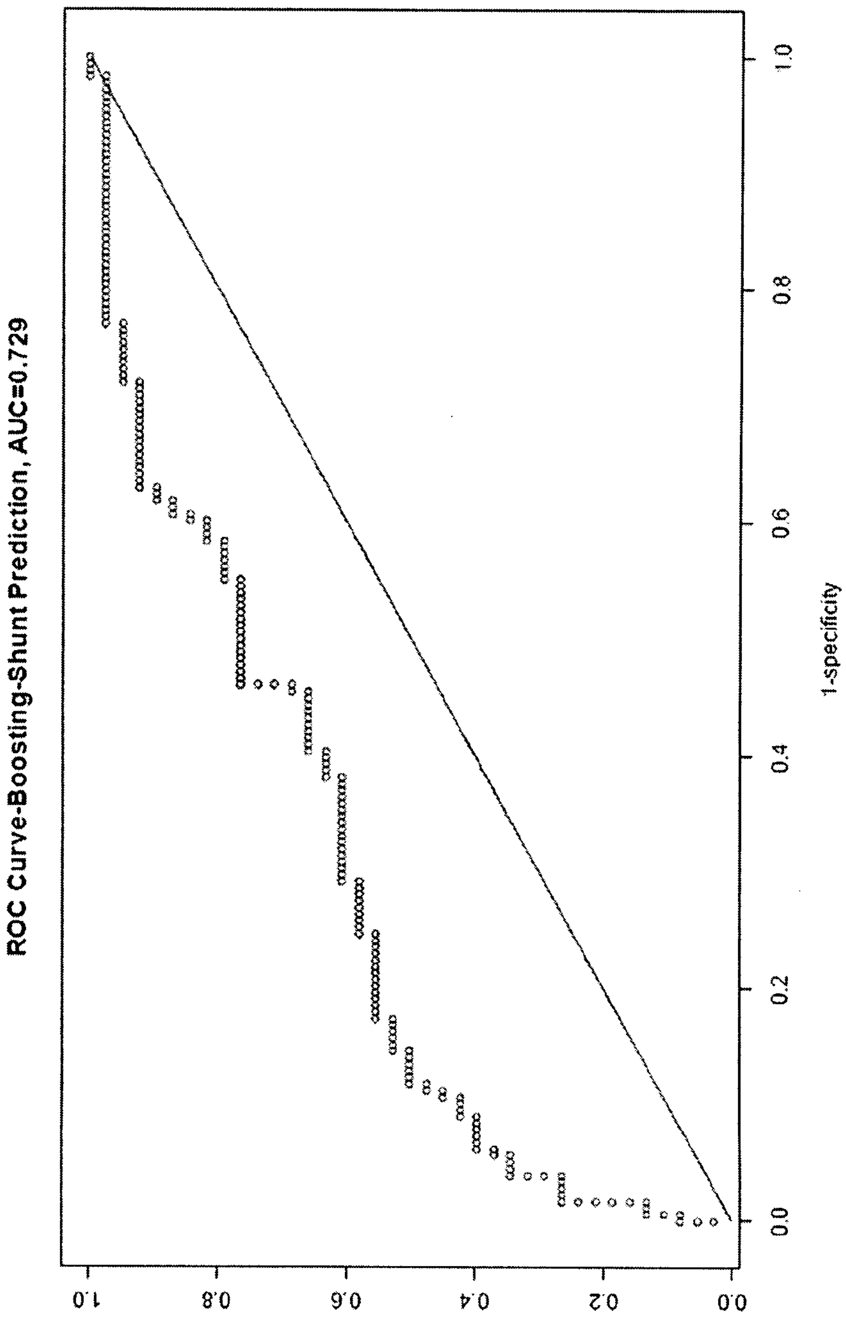
FIG. 16 illustrates an AuROC graph of the boosted trees algorithm for shunting.
Figure 17:
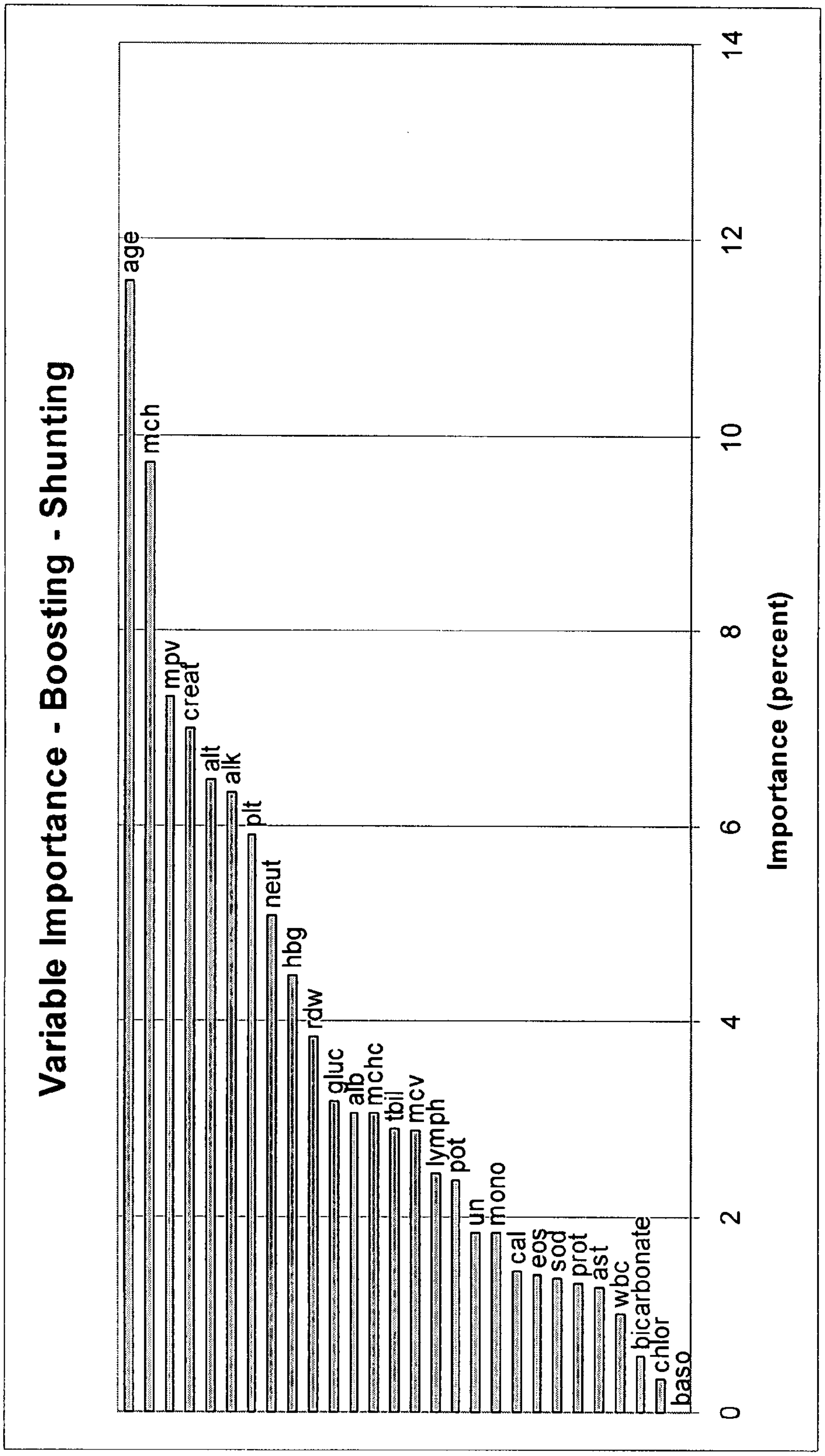
FIG. 17 illustrates a variable importance graph for a set of inputs identifying the boosted trees algorithm for shunting.

The tree boosting approach for clinical response resulted in an AuROC of 0.821 (FIG. 10). The tree boosting approach also provides variable importance numbers as illustrated in FIG. 11 (graph form) and FIG. 12 (table form). The tree boosting approach for adherence or non-compliance resulted in an AuROC of 0.806 (FIG. 13) having variable importance illustrated in FIG. 14 (graph form) and 15 (table form). The tree boosting approach for shunting resulted in an AuROC of 0.729 (FIG. 16) having variable importance illustrated in FIGS. 17 (graph form) and 18 (table form).

Random Forest

Figure 19:
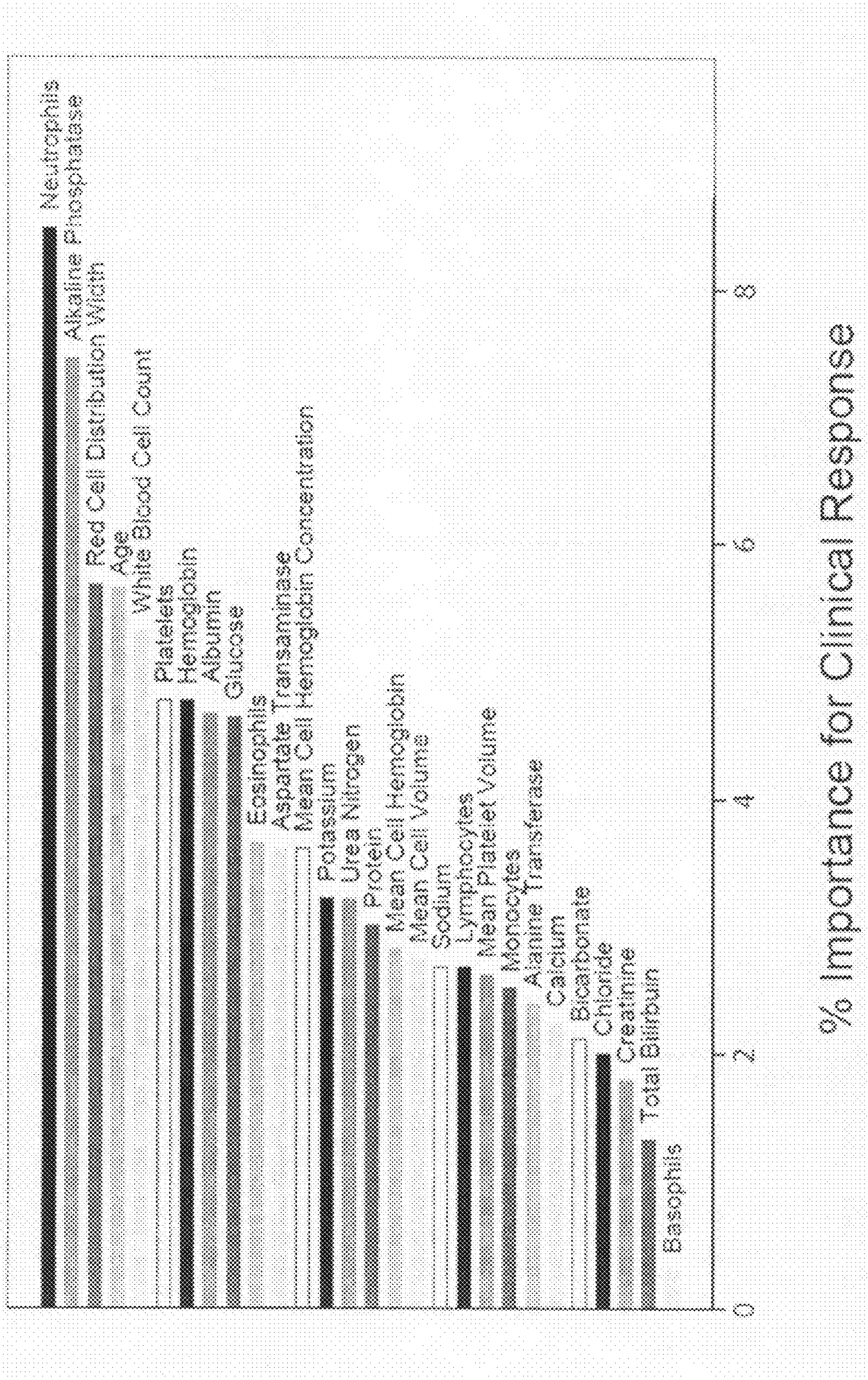
FIG. 19 illustrates a variable importance graph for a set of inputs identifying a random forest generated model for clinical response of thiopurine treatment.
Figure 21:
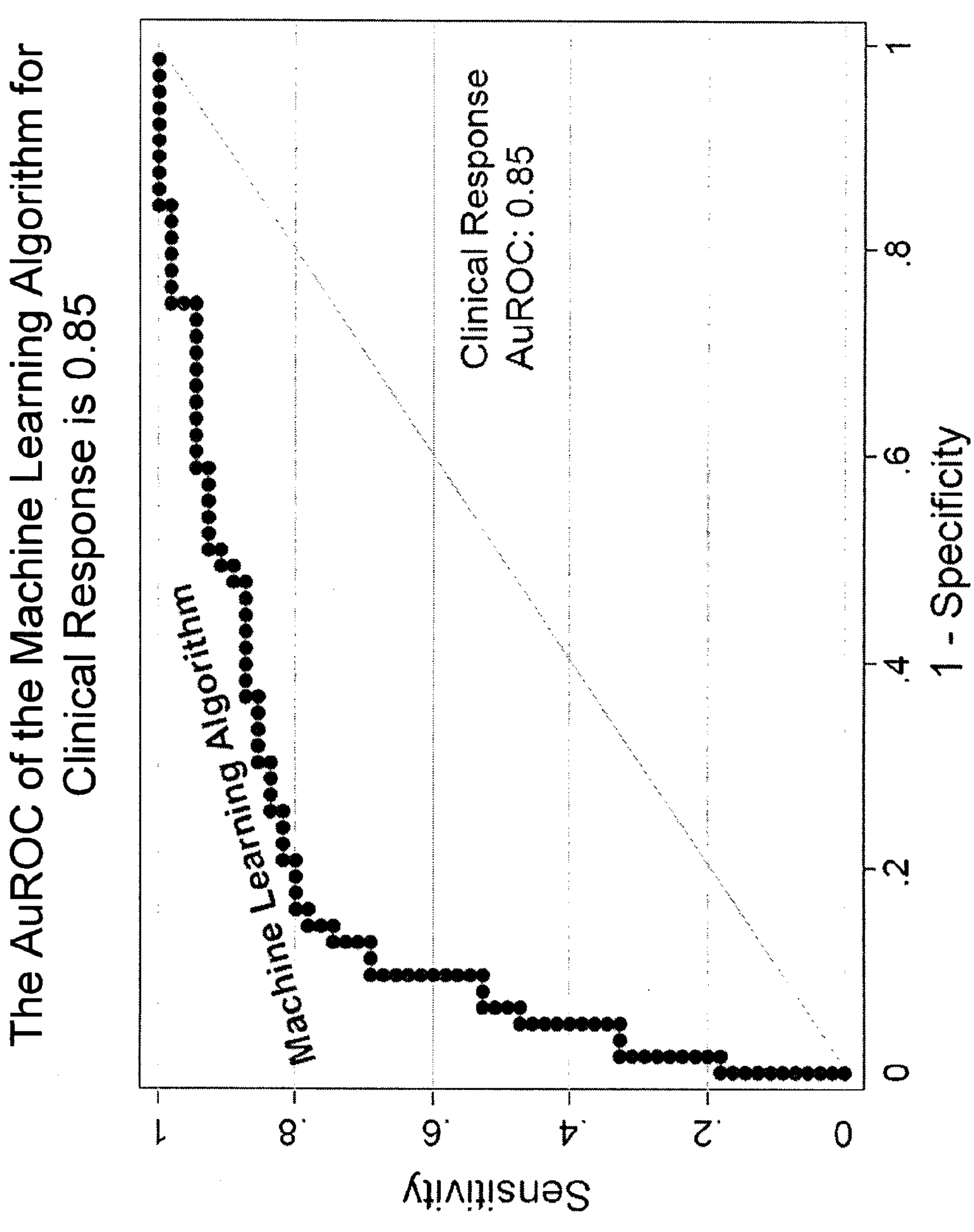
FIG. 21 illustrates an AuROC graph of the random forest algorithm for clinical response.

Random forest modeling may be used to produce algorithms that have similar variable importance results as the boosted tree modeling except with a greater AuROC in the model development data set and in the model validation data set. The effectiveness of the algorithm generated by the random forest model in predicting clinical response is illustrated in FIGS. 19-21. The variable importance of each of the variables is shown in graph form in FIG. 19. The variable importance percentages are listed in table form in FIG. 20. FIG. 21 illustrates an receiver operating characteristic (ROC) curve for the algorithm.

FIG. 21 illustrates that the random forest algorithm using laboratory values and patient age differentiated clinical response in the model validation data set with an area under the ROC curve (AuROC) of 0.85 (95% CI: 0.79 to 0.92). In comparison, 6-TGN levels differentiated clinical response with an AuROC of 0.59 (95% CI: 0.55 to 0.64). The difference between the two areas was highly significant, with a p value of <0.001. It should be noted, that contrary to the so-called "expert" approach that relies on MCV and white blood cell count, the most important independent variables of differentiating clinical responders from non-responders were: age, neutrophil count, red cell distribution width (rdw), hemoglobin, and platelets (see FIGS. 19-21). Also, adding the 6-TGN independent variable to the model did not improve the AuROC of the random forest model. It was 0.85 (95% CI 0.80 to 0.92).

While the complete set of variables for blood count and blood chemistry may be used to derive a first algorithm, a subset of the variables may be used to develop additional algorithms. For example, a subset of the variables may be selected based on the variable importance to generate an algorithm for implementation in testing. Lesser number of variables inputted into the random forest generation model may produce simpler algorithms.

It should be noted that the random forest machine learning approach as well as any of the more sophisticated tree generating approaches (including boosted trees), may produce very complex algorithms (e.g., huge sets of if-then conditions) that can be applied to future cases with computer code, but it is difficult to illustrate the 10,000 or more decision trees in graphical form for inclusion in an application. Instead, the selection of variables used as inputs into any of the regression and classification tree techniques to generate an algorithm and/or the relative importance of the variables also uniquely identify the algorithm. Alternatively, a graph of variable importance percentages can be used to uniquely characterize each algorithm. In fact, both the ratio and the ranges of the variable importance percentages uniquely identify the set of decision trees or algorithms produced by the random forest model. For example, while only a subset of the total list of variables may be used in generating further algorithms, the ratios of relative importance between the remaining variables remains roughly the same, and can be gauged based on the values provided in a variable importance table such as FIG. 20. Variable importance tolerances for all results in this application may be about 20-30 percent, while the tolerances on variable importance ratios may be about 40-60 percent.

Figure 22:
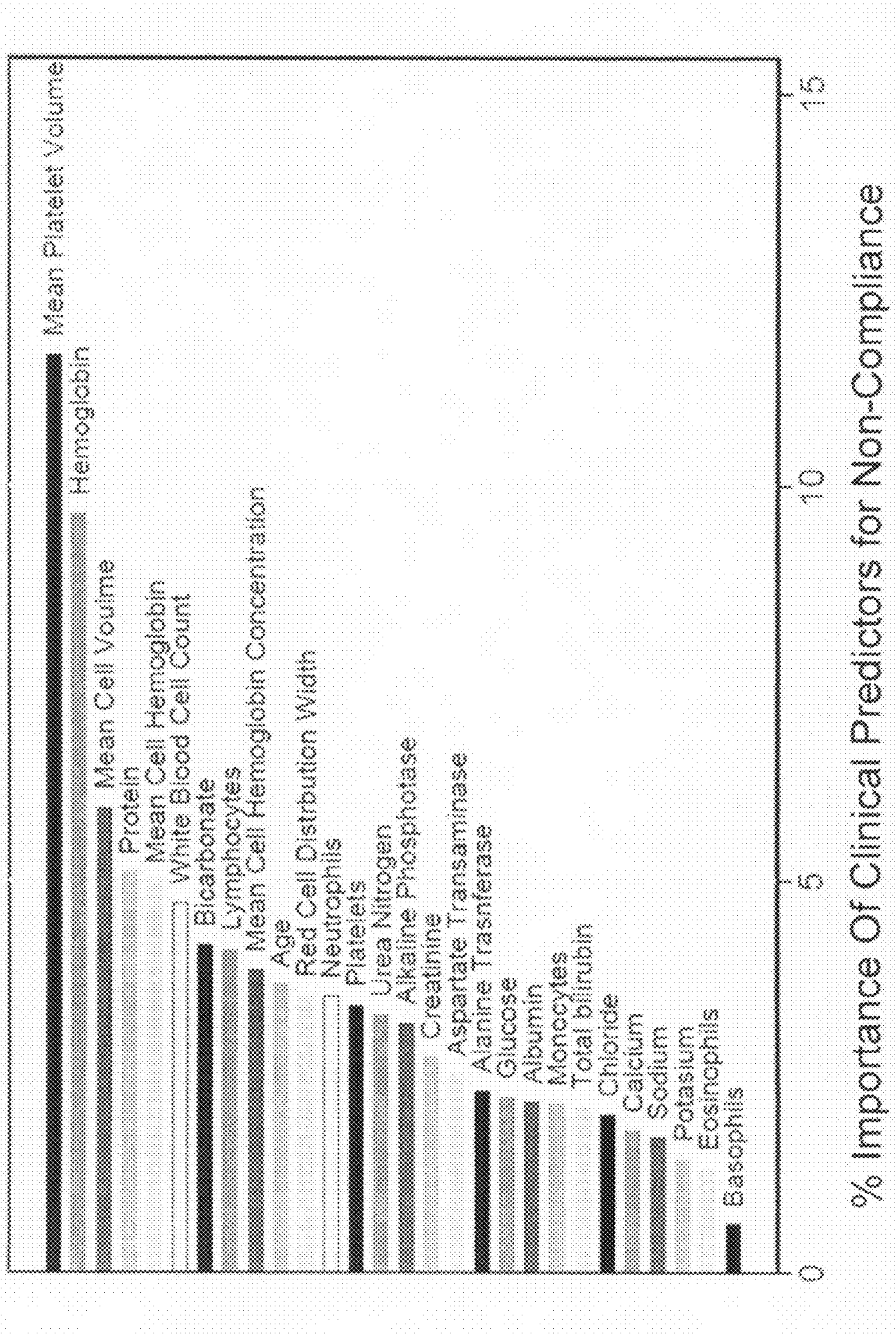
FIG. 22 illustrates a variable importance graph for a set of inputs identifying a random forest generated model for adherence (non-compliance) to thiopurine treatment.
Figure 25:
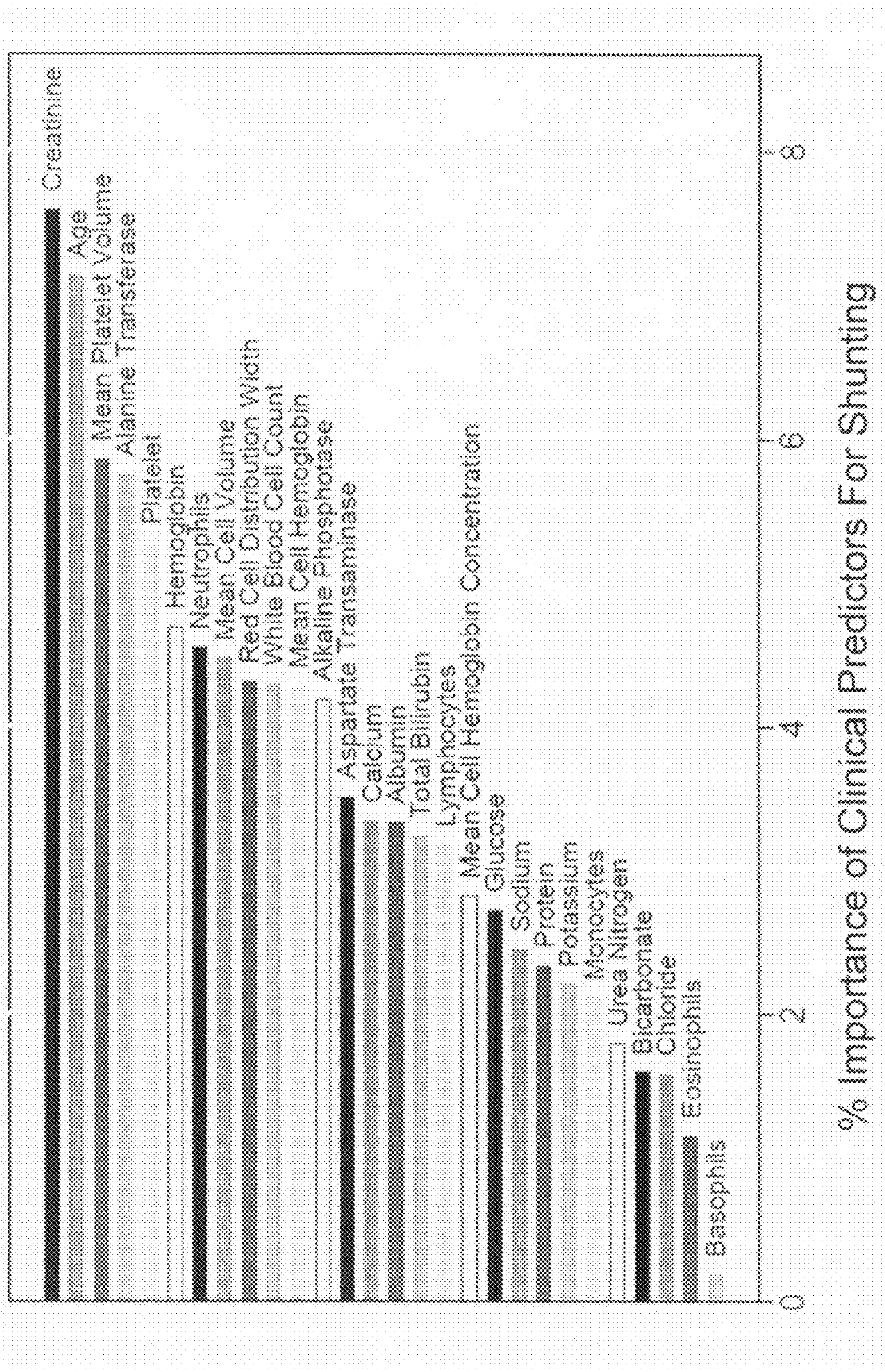
FIG. 25 illustrates a variable importance graph for a set of inputs identifying a random forest generated model for shunting to thiopurine treatment.

Any random forest tree generated according to a data set is suitable according to the present invention, but will be characterized by relative variable importances substantially the same as those displayed in FIGS. 19, 22 and 25 (displayed in tabular form in FIGS. 20, 23 and 26). For example, if all of the variables depicted in FIG. 19 are used, the relative importance of each variable will be about the same percentage within a range of about 25 percent (either lower or higher). As another example, if only 10 of the variables depicted in FIG. 19 are used, the relative importance of one variable to another (e.g. the ratio of the importance of one variable divided by the importance of the other variable) will remain substantially the same, where the ratios differ by only about 7%.

Figure 24:
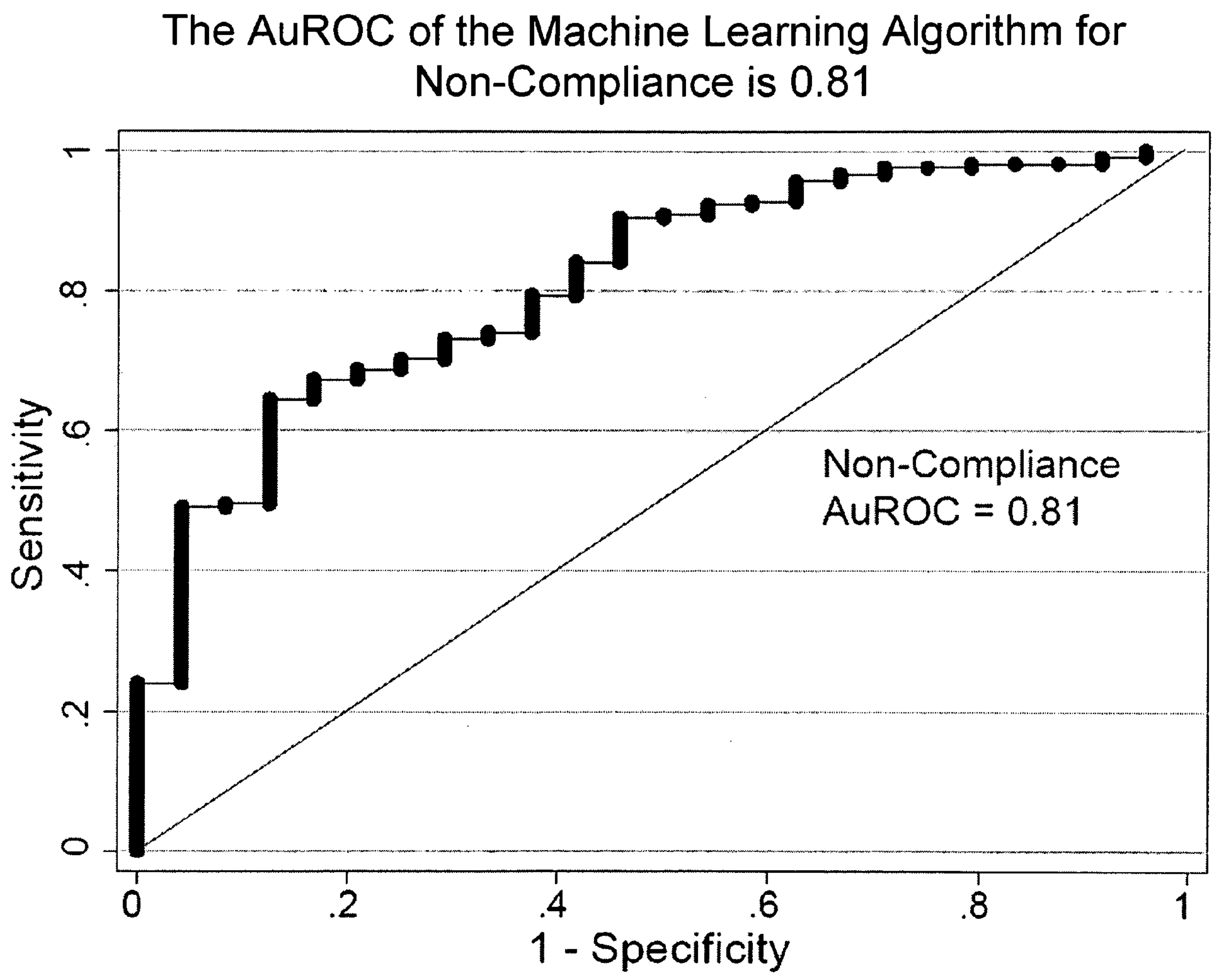
FIG. 24 illustrates an AuROC graph of the random forest algorithm for adherence.
Figure 27:
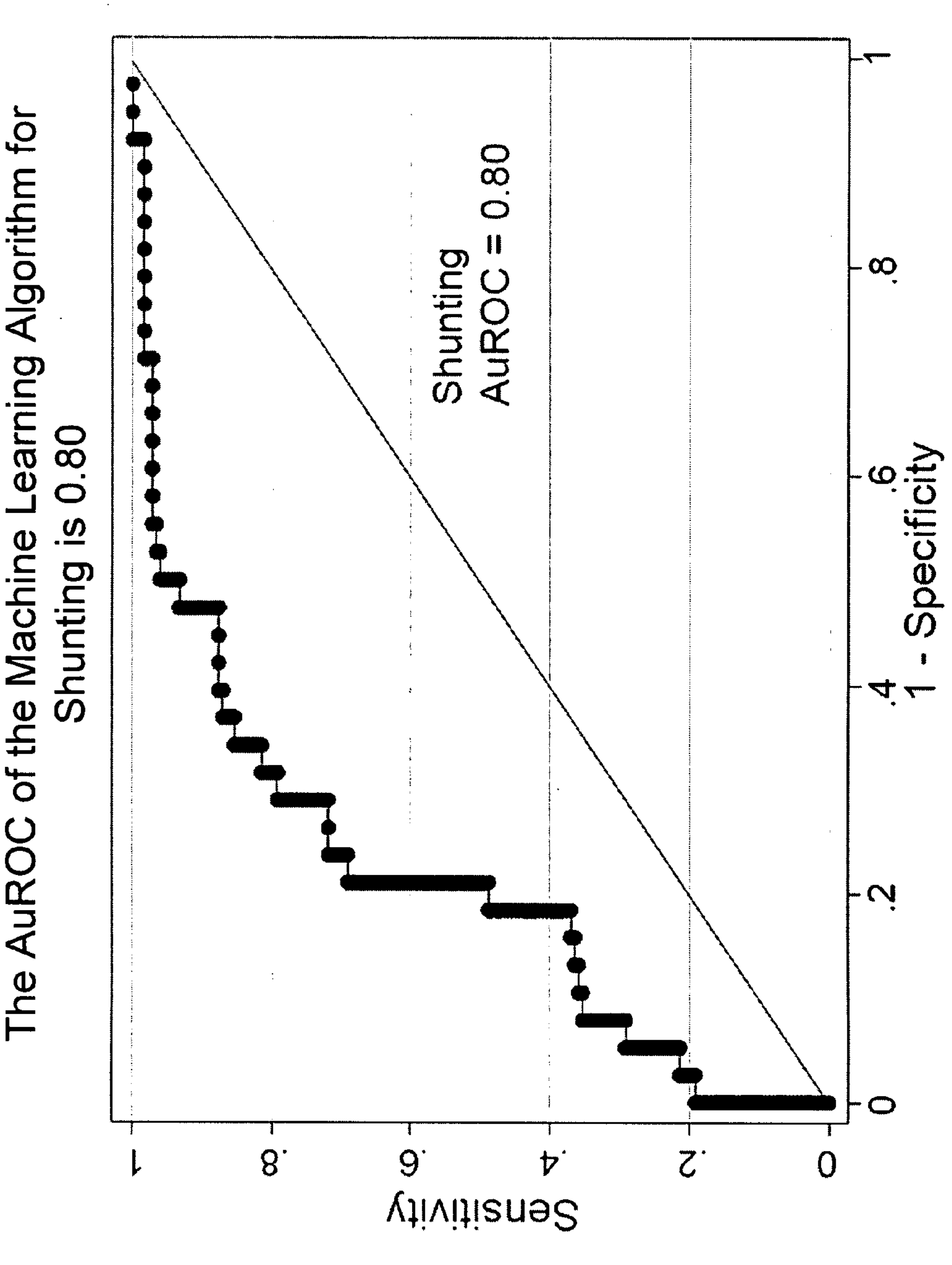
FIG. 27 illustrates an AuROC graph of the random forest algorithm for shunting.

The same set of independent variables were used in a random forest model to determine variable importance in predicting adherence and shunting. FIG. 22 (graphical form) and FIG. 23 (table form) illustrate the importance of the variables used in predicting non-compliance. FIG. 25 (graphical form) and FIG. 26 (table form) illustrate the importance of the variables used in predicting shunting. The resulting random forest generated algorithm using laboratory values and patient age differentiated thiopurine noncompliance with an AuROC of 0.81 (95% CI 0.76 to 0.86) (FIG. 24), and thiopurine shunters with an AuROC of 0.80 (95% CI 0.74 to 0.85) (FIG. 27).

RuleFit

Figure 28:
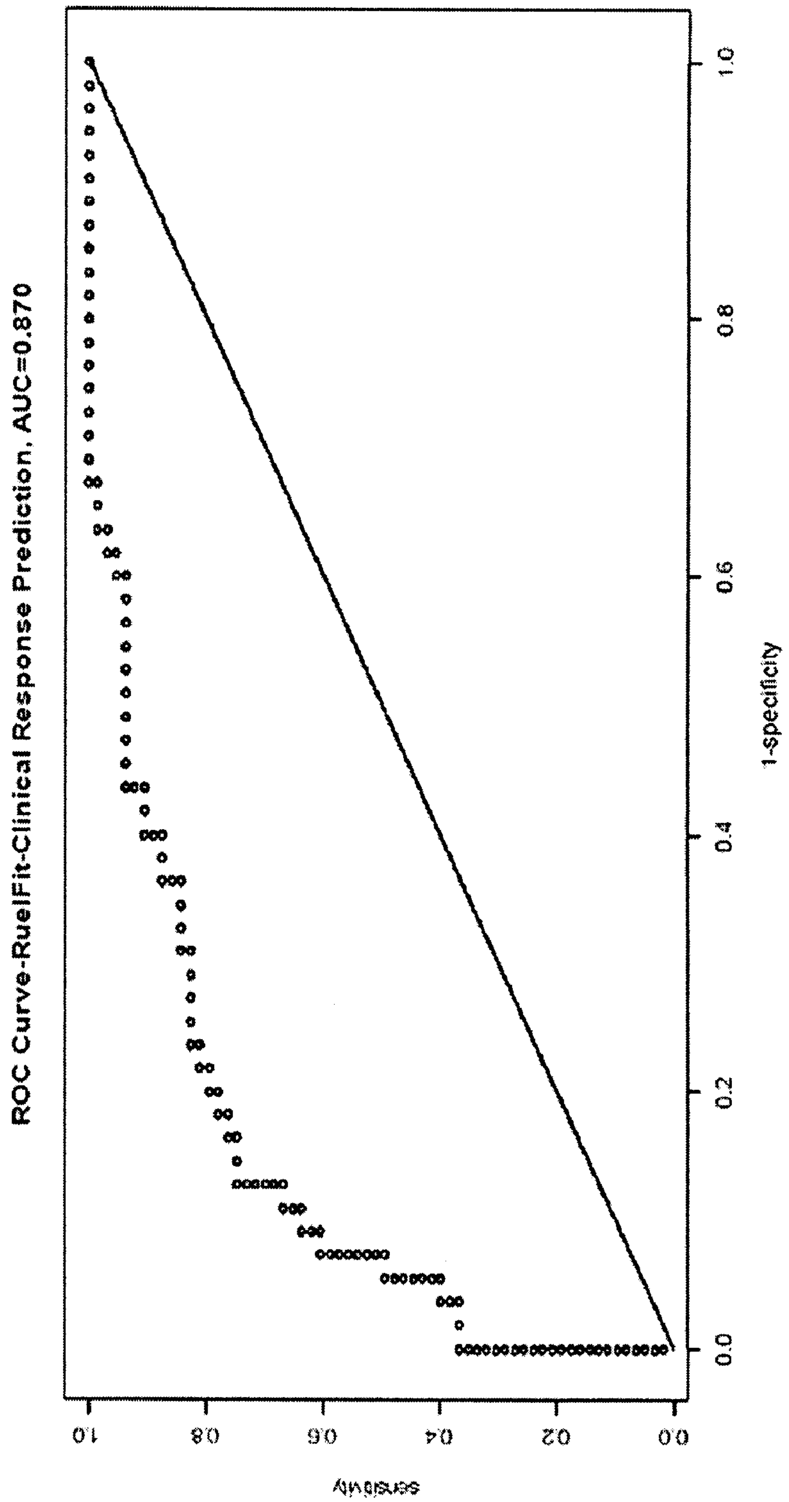
FIG. 28 illustrates an AuROC graph of a RuleFit algorithm for clinical response.
Figure 29:
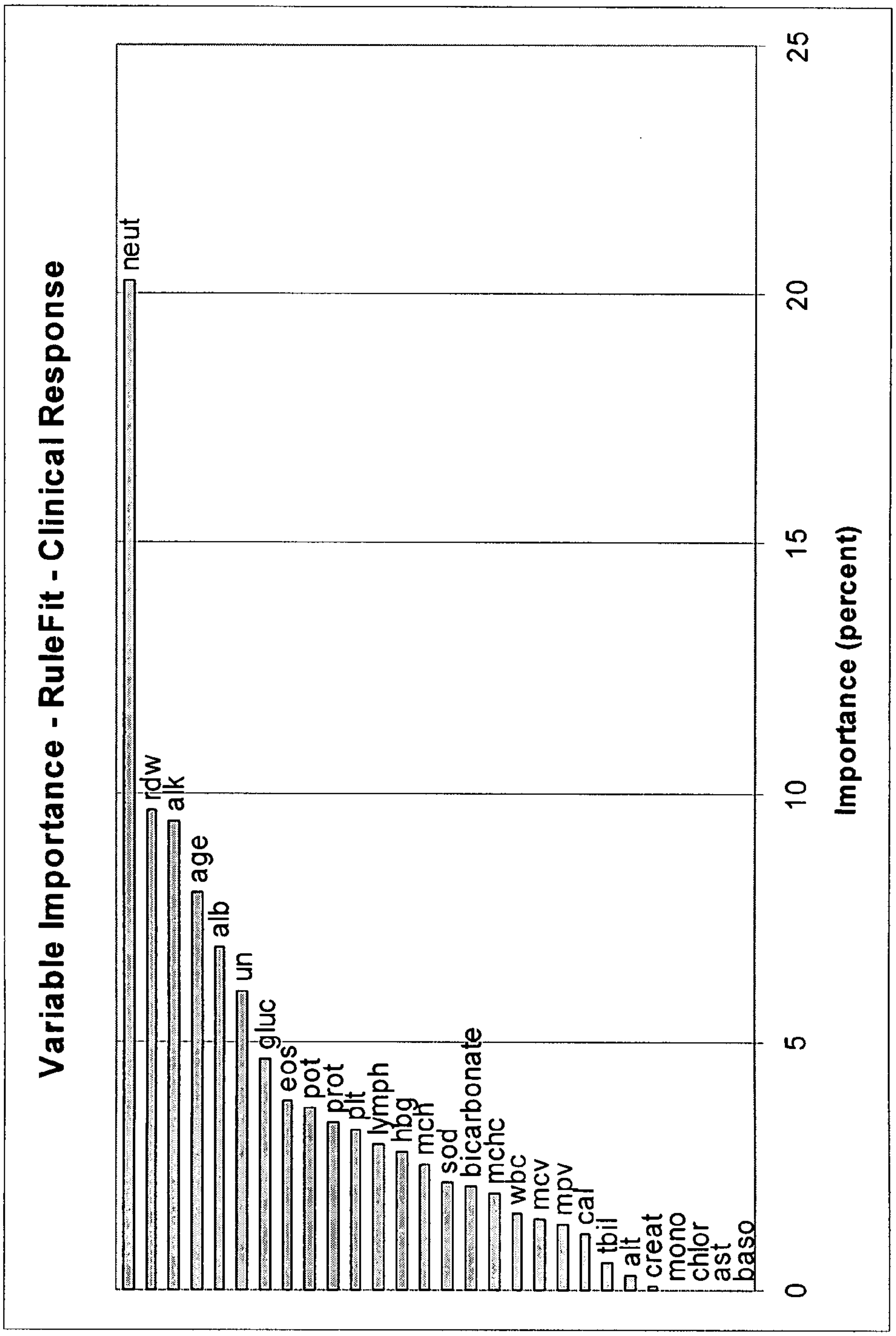
FIG. 29 illustrates a variable importance graph for a set of inputs identifying RuleFit generated model for clinical response to thiopurine treatment.
Figure 31:
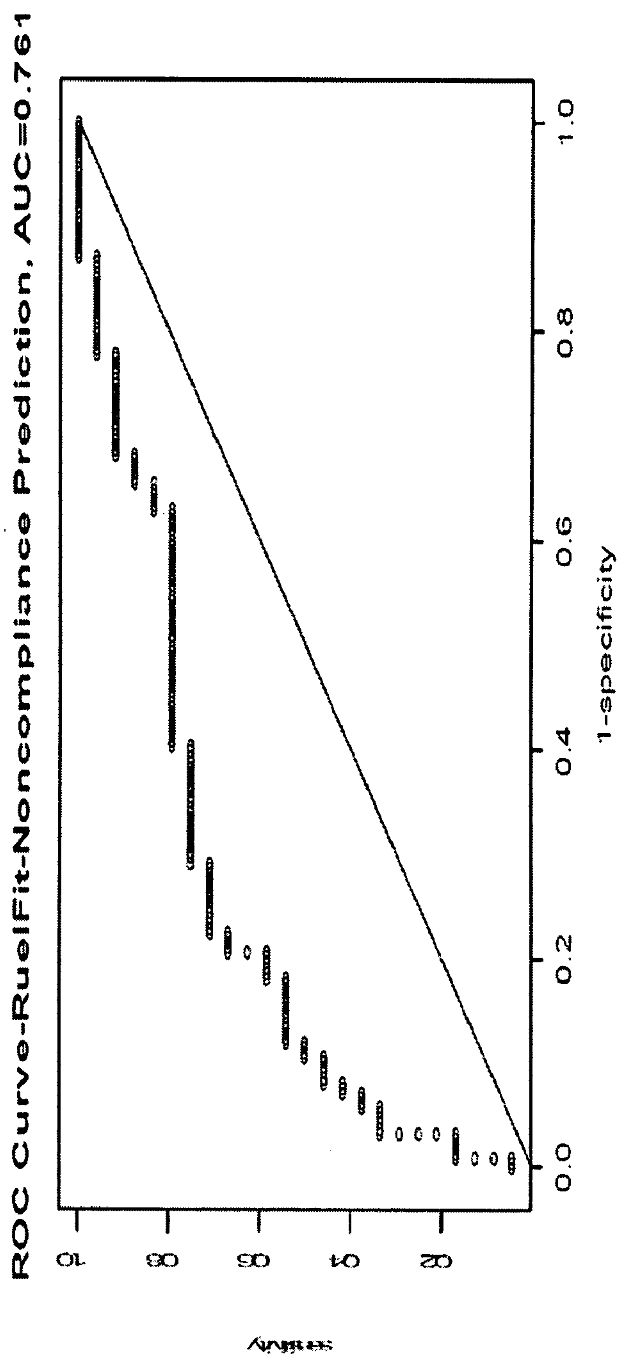
FIG. 31 illustrates an AuROC graph of a RuleFit algorithm for adherence.
Figure 32:
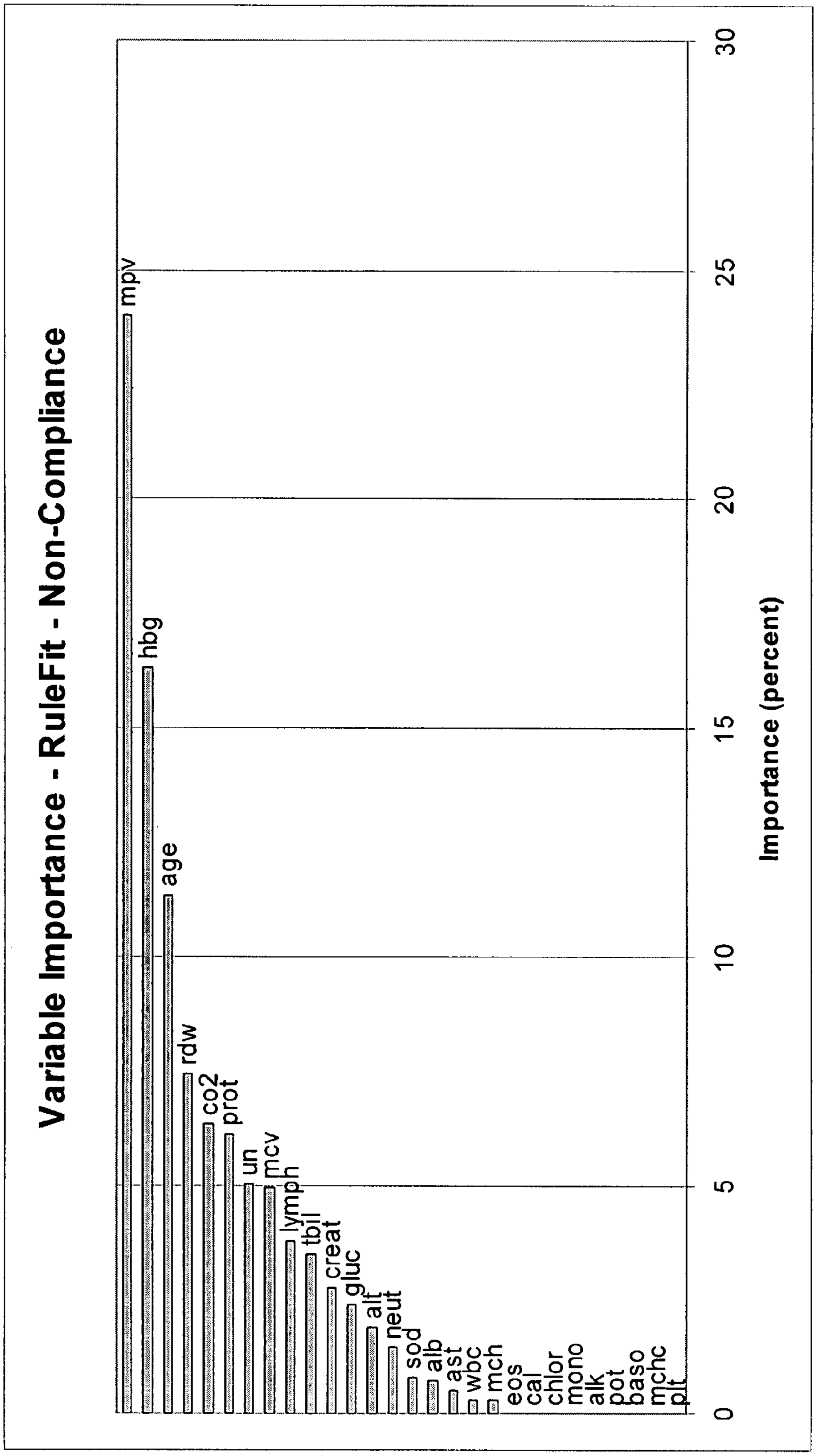
FIG. 32 illustrates a variable importance graph for a set of inputs identifying RuleFit generated model for adherence to thiopurine treatment.
Figure 34:
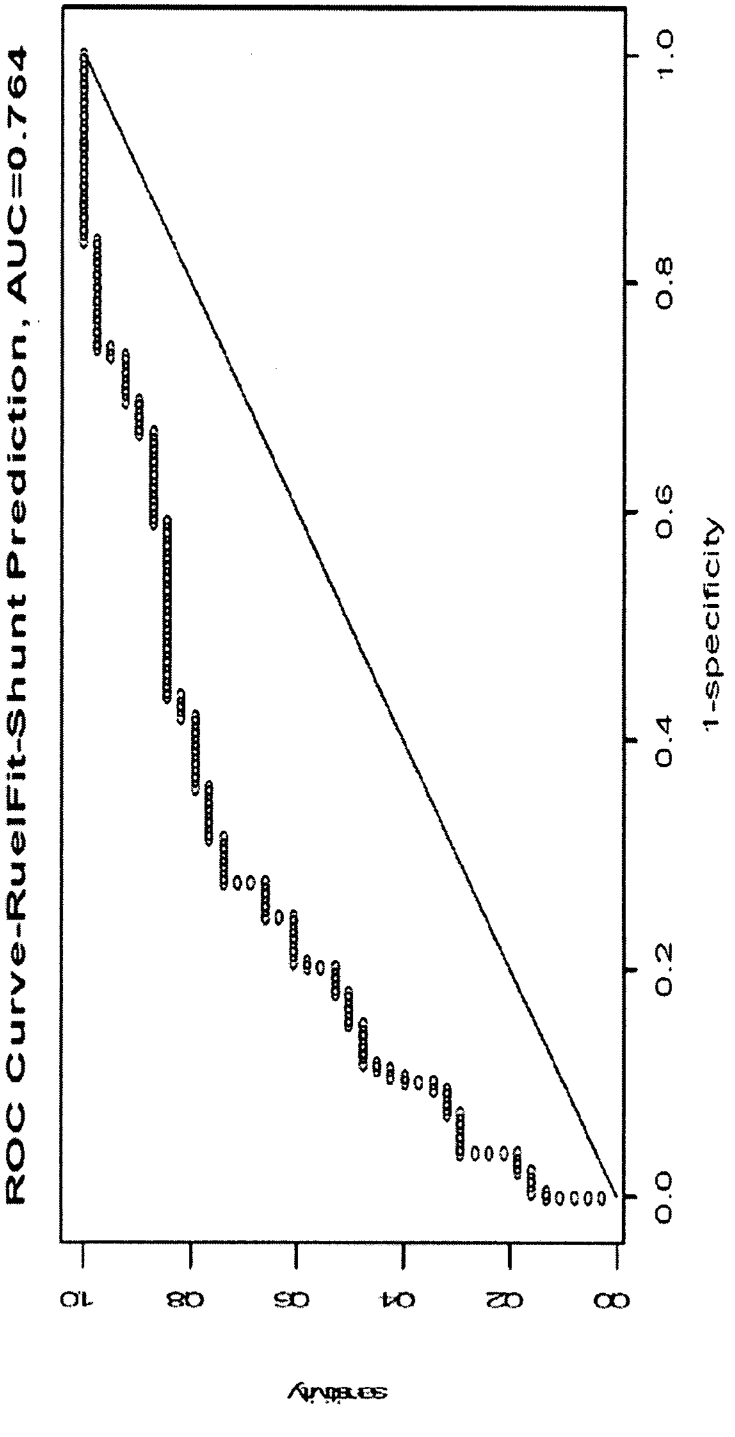
FIG. 34 illustrates an AuROC graph of a RuleFit algorithm for shunting.
Figure 35:
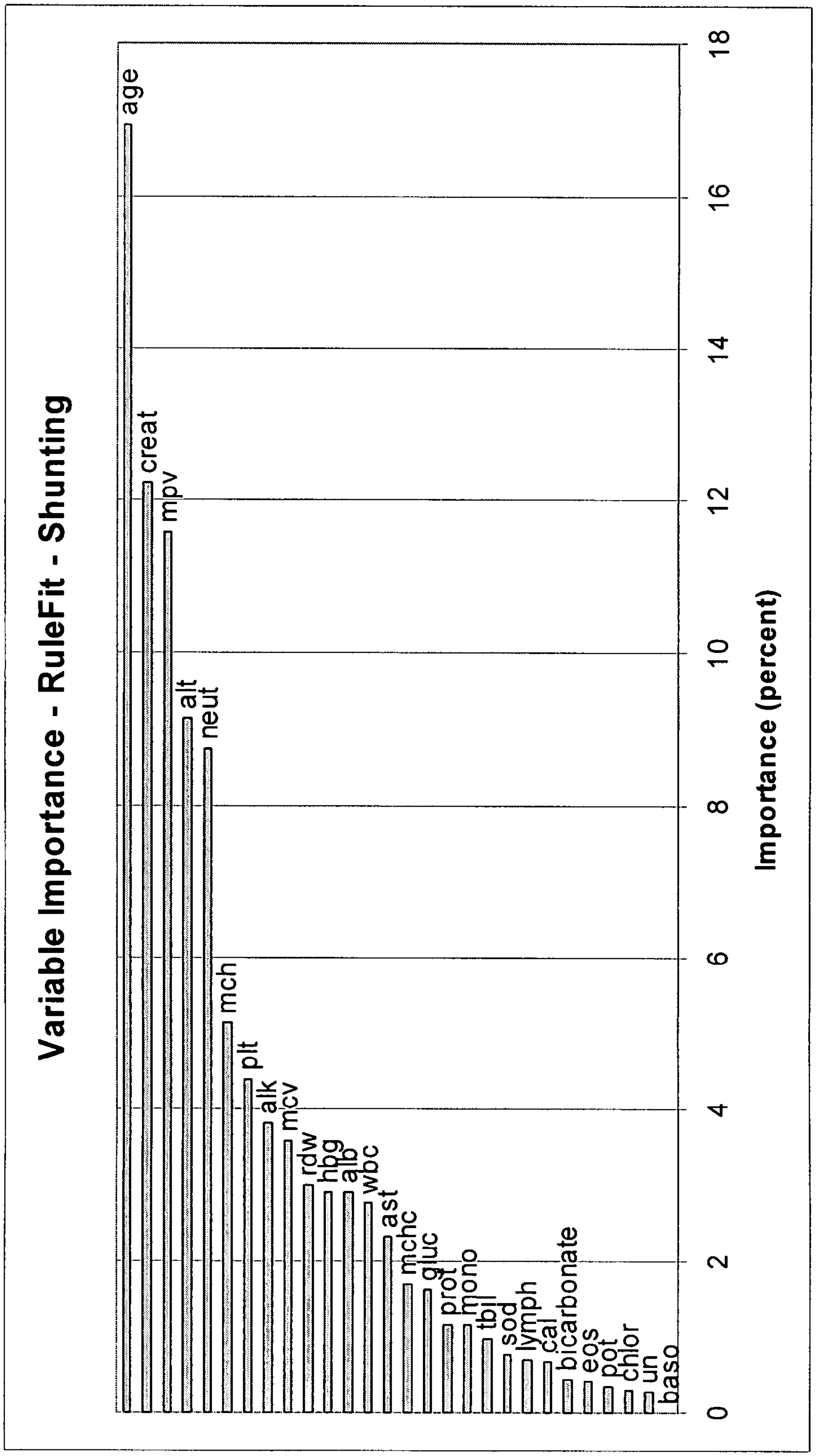
FIG. 35 illustrates a variable importance graph for a set of inputs identifying RuleFit generated model for shunting to thiopurine treatment.

The RuleFit approach for clinical response resulted in an AuROC of 0.870 (FIG. 28). The RuleFit approach also provides a listing of variable importance as illustrated in FIG. 29 (graph form) and FIG. 30 (table form). The RuleFit approach for adherence or non-compliance resulted in an AuROC of 0.761 (FIG. 31) having variable importance illustrated in FIG. 32 (graph form) and 33 (table form). The RuleFit approach for shunting resulted in an AuROC of 0.764 (FIG. 34) having variable importance illustrated in FIGS. 35 (graph form) and 36 (table form).

Logistic Regression Method

To further simplify the algorithms, a stepwise logistic regression may be performed on the entire data set or a subset of the data set to develop algorithms to differentiate each of the three dependent variables. The logistic models may be evaluated using area under ROC curve (AuROC) graphs evaluated for their calibration with Hosmer-Lemeshow tables. The 6-TGN variable may be added to the logistic laboratory algorithm for clinical response, to determine if it would improve the model based on standard laboratory results.

The multivariate logistic regression model may yield a number of statistically significant variables for clinical response, as illustrated in table form in FIG. 12, including white blood cell count (wbc), red cell distribution width (rdw), eosinophil count (eos), albumin level (alb) and patient age. It should be noted that the addition of the 6-TGN independent variable did not improve the model, and the 6-TGN variable was not statistically significant in this multivariate model, with a p value of 0.324.

The values listed as odds-ratio in the table of FIG. 37 may be used as coefficients in the following regression equation to produce simple estimates of clinical response:

clinical response probability=1/(1+exp(−[constant+coefficient1(white blood cell count)+coefficient2(red blood cell volume distribution width)+coefficient3(eosinophil count)+coefficient4(albumin level)+coefficient5(age of patient)])), wherein coefficient1 is about 0.754,
coefficient2 is about 0.804,
coefficient3 is about 8.051,
coefficient4 is about 2.903, and
coefficient5 is about 0.972.

The multivariate logistic regression model to explain noncompliance was constructed and yielded a number of statistically significant variables as illustrated in FIG. 38, including white blood cell count (wbc), patient age, mean corpuscular hemoglobin (mch), neutrophil count (neut) and red cell distribution width (rdw).

The values listed as odds-ratio in the table of FIG. 38 may be used as coefficients in the following regression equation to produce simple estimates of non-compliance:

probability=1/(1+exp(−[constant+coefficient1(white blood cell count)+coefficient2(age of patient)+coefficient3(mean corpuscular hemoglobin)+coefficient4(neutrophil count)+coefficient5(red blood cell volume distribution width)])), wherein coefficient1 is about 1.756,
coefficient2 is about 1.049,
coefficient3 is about 0.666,
coefficient4 is about 0.578, and
coefficient5 is about 0.656.

A multivariate logistic regression model to help explain shunting was constructed, and yielded a number of statistically significant variables as illustrated in FIG. 39, including eosinophils (eos), creatinine (creat), lymphocytes (lymph), and mean corpuscular hemoglobin (mch).

The values listed as odds-ratio in the table of FIG. 39 may be used as coefficients in the following regression equation to produce simple estimates of shunting:

probability=1/(1+exp(−[constant+coefficient1(eosinophil count)+coefficient2(creatinine level)+coefficient3(lymphocyte count)+coefficient4(mean corpuscular hemoglobin content)])), wherein coefficient1 is about 0.104,
coefficient2 is about 0.059,
coefficient3 is about 1.518, and
coefficient4 is about 1.149.

Computer Implementation

Figure 40:
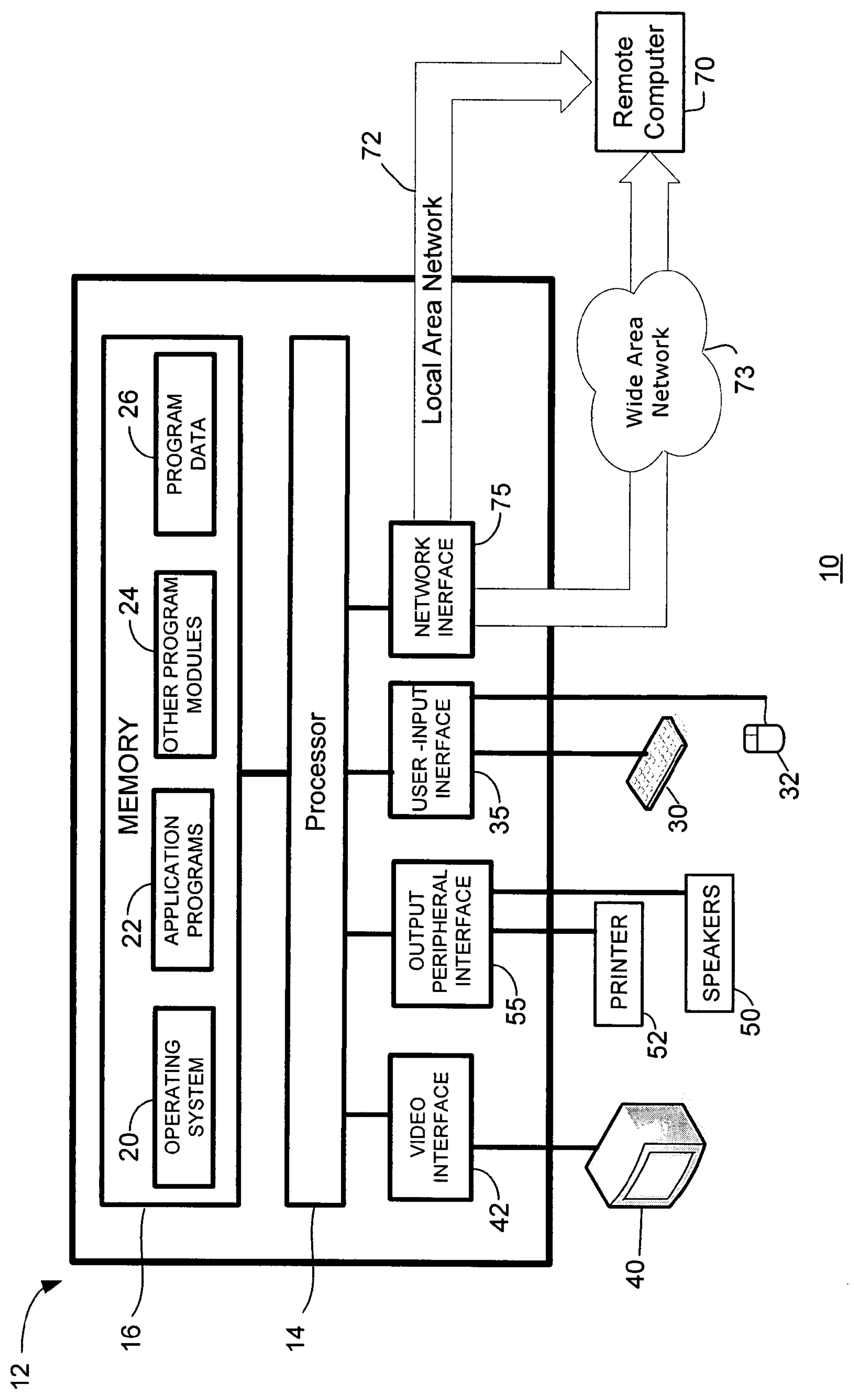
FIG. 40 illustrates a block diagram of a computing system that may operate in accordance with the claims.

The classification and regression tree approaches and logistic regression may be coded as a program for execution on a computing device such as that illustrated in FIG. 40. Generally, FIG. 40 illustrates an example of a suitable computing system environment 10 that may operate to display and provide the user interface described by this specification. It should be noted that the computing system environment 10 is only one example of a suitable computing environment and is not intended to suggest any limitation as to the scope of use or functionality of the method and apparatus of the claims. Neither should the computing environment 10 be interpreted as having any dependency or requirement relating to any one component or combination of components illustrated in the exemplary operating environment 10.

With reference to FIG. 40, an exemplary system for implementing the blocks of the claimed method and apparatus includes a general purpose computing device in the form of a computer 12. Components of computer 12 may include, but are not limited to, a processing unit 14 and a system memory 16. The computer 12 may operate in a networked environment using logical connections to one or more remote computers, such as a remote computer 70, via a local area network (LAN) 72 and/or a wide area network (WAN) 73 via a modem or other network interface 75.

Computer 12 typically includes a variety of computer readable media that may be any available media that may be accessed by computer 12 and includes both volatile and nonvolatile media, removable and non-removable media. The system memory 16 includes computer storage media in the form of volatile and/or nonvolatile memory such as read only memory (ROM) and random access memory (RAM). The ROM may include a basic input/output system (BIOS). RAM typically contains data and/or program modules that include operating system 20, application programs 22, other program modules 24, and program data 26. The computer 12 may also include other removable/non-removable, volatile/nonvolatile computer storage media such as a hard disk drive, a magnetic disk drive that reads from or writes to a magnetic disk, and an optical disk drive that reads from or writes to an optical disk.

A user may enter commands and information into the computer 12 through input devices such as a keyboard 30 and pointing device 32, commonly referred to as a mouse, trackball or touch pad. Other input devices (not illustrated) may include a microphone, joystick, game pad, satellite dish, scanner, or the like. These and other input devices are often connected to the processing unit 14 through a user input interface 35 that is coupled to a system bus, but may be connected by other interface and bus structures, such as a parallel port, game port or a universal serial bus (USB). A monitor 40 or other type of display device may also be connected to the processor 14 via an interface, such as a video interface 42. In addition to the monitor, computers may also include other peripheral output devices such as speakers 50 and printer 52, which may be connected through an output peripheral interface 55.

Generally, the tree classification models, such as random forest, may be coded in R language (a statistical programming language developed and distributed by the GNU system) or any other computing language for execution on computer 12. Once the classification model program (e.g., random forest) is loaded on to computer 12, the program may be executed on observed data, such as the training set of patient results indicating clinical response and values for blood counts, blood chemistry, and patient age. This observed data may be loaded on to any of the computer storage devices of computer 12 to generate an appropriate tree algorithm (e.g., using CART, boosted trees, random forest, RuleFit) or logistic regression formula. Once generated, the tree algorithm, which may take the form of a large set of if-then conditions, may then be coded using any general computing language for test implementation. For example, the if-then conditions can be capture using C/C++ and compiled to produce an executable, which, when run, accepts new patient data and outputs a calculated prediction on any one of clinical response, adherence, or shunting. The output of the executable program may be displayed on a display (e.g., a monitor 40) or sent to a printer 52. The output may be in the form of a graph or table indicating the prediction or probability value along with related statistical indicators such as p-values. In one embodiment, R language may be used to run the random forest and boosted trees approaches. Alternatively, the program executing the tree classification model may also be programmed to accept future inputs into its generated tree algorithm for producing a prediction of the independent variable (e.g., clinical response).

What is claimed:

1. A method of determining the effectiveness of thiopurine treatment in a patient receiving the thiopurine treatment for inflammatory bowel disease (IBD) comprising:

receiving on a computer device a set of data inputs related to characteristics of a patient receiving a thiopurine treatment for inflammatory bowel disease; and calculating on the computer device a clinical response probability based on the set of data inputs using an algorithm that applies a weight to each data input of the set of data inputs, wherein each weight relates to a quantified importance of a particular data input associated with a fixed set of patient data from patients receiving a thiopurine treatment for inflammatory bowel disease in which the clinical response of the patients is known, wherein the set of data comprises at least three data inputs selected from the group consisting of hemoglobin (HGB), hematocrit (HCT), platelet count (PLT), red blood cell count (RBC), mean corpuscular hemoglobin (MCH), mean corpuscular hemoglobin concentration (MCHC), red cell distribution width (RDW), mean platelet volume (MPV), sodium level (SOD), potassium level (POT), chloride (CHLOR), carbon dioxide (CO2), urea nitrogen (UN), creatinine level (CREAT), glucose level (GLUC), calcium level (CAL), protein level (PROT), albumin level (ALB), aspartate transaminase (AST), alanine transaminase (ALT), alkaline phosphatase (ALK), bilirubin total (TBIL), neutrophil count (NEUT), monocyte count (MONO), basophil count (BASO), and age of patient (Age).

2. The method of claim 1, wherein the set of data inputs include at least four of red blood cell volume distribution width (RDW), eosinophil count (EOS), albumin level (ALB), alkaline phosphatase level (ALK), sodium level (SOD), mean corpuscular hemoglobin content (MCH), neutrophil count (NEUT), platelet count (PLT), creatinine level (CREAT), hematocrit (HCT), or age of patient (AGE).

3. The method of claim 1, wherein the probability is calculated using an algorithm generated by a modeling analysis selected from the group consisting of a logistic regression analysis, a classification and regression tree (CART) analysis, a random forest analysis, RuleFit, and a boosted tree regression.

4. The method of claim 1, wherein determining the clinical response probability is calculated based on a statistical regression model, and the set of data inputs for calculating the clinical response probability includes white blood cell count (WBC), red blood cell volume distribution width (RDW), eosinophil count (EOS), albumin level (ALB), alkaline phosphatase level (ALK), sodium level (SOD), and age of patient.

5. The method of claim 1, wherein determining the adherence probability is calculated based on a model derived from a logistic regression using white blood cell count (WBC), mean corpuscular hemoglobin content (MCH), neutrophil count (NEUT), red blood cell volume distribution width (RDW), and age of patient.

6. The method of claim 1, wherein determining the shunting probability is calculated based on a model derived from a logistic regression using platelet count (PLT), red blood cell volume distribution width (RDW), eosinophil count (EOS), albumin level (ALB), creatinine level (CREAT), lymphocyte count (LYMPH), mean corpuscular hemoglobin content (MCH), and hematocrit (HCT).

7. A method of determining the effectiveness of thiopurine treatment in a patient receiving the thiopurine treatment for inflammatory bowel disease (IBD) comprising:

receiving on a computer device a set of data inputs related to characteristics of a patient receiving a thiopurine treatment for inflammatory bowel disease; and calculating on the computer device a clinical response probability based on the set of data inputs using an algorithm that applies a weight to each data input of the set of data inputs, wherein each weight relates to a quantified importance of a particular data input associated with a fixed set of patient data from patients receiving a thiopurine treatment for inflammatory bowel disease in which the clinical response of the patients is known, wherein the set of data inputs comprises white blood cell count, red blood cell volume distribution width, eosinophile count, albumin level, and age patent, and wherein the clinical response probability is calculated as probability=1/(1+exp(−[constant+coefficient1(white blood cell count)+coefficient2(red blood cell volume distribution width)+coefficient3(eosinophil count)+coefficient4(albumin level)+coefficient 5(age of patient)])), wherein coefficient1 is about 0.754,
coefficient2 is about 0.804,
coefficient3 is about 8.051,
coefficient4 is about 2.903, and
coefficient5 is about 0.972.

8. The method of claim 1, wherein the adherence probability is calculated as probability=1/(1+exp(−[constant+coefficient1(white blood cell count)+coefficient2(age of patient)+coefficient3(mean corpuscular hemoglobin content)+coefficient4(neutrophil count)+coefficient5 (red blood cell volume distribution width)])), wherein coefficient1 is about 1.756,
coefficient2 is about 1.049,
coefficient3 is about 0.666,
coefficient4 is about 0.578, and
coefficient5 is about 0.656.

9. The method of claim 1, wherein the shunting probability is calculated as probability=1/(1+exp(−[constant+coefficient1(eosinophil count)+coefficient2(creatinine level)+coefficient3(lymphocyte count)+coefficient4(mean corpuscular hemoglobin content)])), wherein coefficient1 is about 0.104,
coefficient2 is about 0.059,
coefficient3 is about 1.518, and
coefficient4 is about 1.149.

* * * * *